US008562515B2

(12) United States Patent
Nishino

(10) Patent No.: US 8,562,515 B2
(45) Date of Patent: Oct. 22, 2013

(54) CAPSULE ENDOSCOPE, CAPSULE ENDOSCOPIC SYSTEM, AND ENDOSCOPE CONTROL METHOD

(75) Inventor: Naoyuki Nishino, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1263 days.

(21) Appl. No.: 12/046,140

(22) Filed: Mar. 11, 2008

(65) Prior Publication Data

US 2008/0242926 A1    Oct. 2, 2008

(30) Foreign Application Priority Data

Mar. 28, 2007  (JP) ................................ 2007-083457

(51) Int. Cl.
*A61B 1/04* (2006.01)
*A61B 1/00* (2006.01)
*A61B 1/06* (2006.01)

(52) U.S. Cl.
USPC ........... 600/118; 600/103; 600/117; 600/160; 600/178; 396/322; 396/325

(58) Field of Classification Search
USPC .......... 396/322, 323, 332–335; 600/111, 113, 600/117, 118, 166, 103, 160, 178
See application file for complete search history.

(56) References Cited

U.S. PATENT DOCUMENTS

2003/0208107 A1* 11/2003 Refael .......................... 600/300
2004/0111011 A1*  6/2004 Uchiyama et al. ............ 600/160
2005/0004474 A1*  1/2005 Iddan ............................ 600/476
2005/0054897 A1*  3/2005 Hashimoto et al. ........... 600/118
2006/0178557 A1*  8/2006 Mintchev et al. ............. 600/104

FOREIGN PATENT DOCUMENTS

| JP | 2003-070728 A | 3/2003 |
|---|---|---|
| JP | 2004-154176 A | 6/2004 |
| JP | 2004-350963 A | 12/2004 |
| JP | 2005-503182 A | 2/2005 |
| JP | 2006-068534 A | 3/2006 |
| JP | 2006-166990 A | 6/2006 |

OTHER PUBLICATIONS

Notification of Reasons for Refusal, dated Mar. 28, 2012, issued in corresponding JP Application No. 2007-083457, 11 pages in English and Japanese.

* cited by examiner

*Primary Examiner* — Philip R Smith
*Assistant Examiner* — Rynae Boler
(74) *Attorney, Agent, or Firm* — Sughrue Mion, PLLC

(57) ABSTRACT

A capsule endoscope system includes a capsule endoscope and a receiver. The capsule endoscope has plural image pickup units for endoscopic imaging by passing a gastrointestinal tract in a body. The receiver for wireless communication with the capsule endoscope receives and stores image data from the capsule endoscope. The receiver includes a data analyzer for retrieving position relationship data expressing a position relationship of the image pickup units to a target region in the gastrointestinal tract. A CPU of the receiver produces a command signal according to the position relationship data for determining a number of frames of imaging per unit time for respectively the plural image pickup units. The capsule endoscope includes a CPU for controlling operation of the plural image pickup units according to the command signal from the receiver.

20 Claims, 12 Drawing Sheets

CAPSULE ENDOSCOPE, CAPSULE ENDOSCOPIC SYSTEM, AND ENDOSCOPE CONTROL METHOD

BACKGROUND OF THE INVENTION

1. Field of the Invention

The present invention relates to a capsule endoscope, capsule endoscopic system, and endoscope control method. More particularly, the present invention relates to a capsule endoscope in which plural image pickup units are incorporated, and of which handling of acquired images can be facilitated, and a capsule endoscopic system, and endoscope control method.

2. Description Related to the Prior Art

A capsule endoscope is known in the medical field for diagnosis. A small capsule casing of the capsule endoscope contains an image pickup unit, a light source and the like. In the diagnosis, at first a patient is caused to swallow the capsule endoscope. While the light source illuminates a target region on inner surfaces of a gastrointestinal tract in the body, the image pickup unit photographs the target region. Image data are obtained, and transmitted to a receiver. A flash memory in the receiver is accessed to store the image data successively. During or after the inspection, image data are retrieved in a workstation as managing apparatus, for diagnosing images displayed on a display panel.

A single head type of the capsule endoscope includes a single image pickup unit, as widely known in the art. It is likely that lesions of the target region may be missed in the image pickup due to the single direction of the image pickup. In view of preventing the missing, a multi head type of the capsule endoscope including a plurality of image pickup units is suggested, for example U.S. Pat. Pub. 2005/004474 (corresponding to JP-A 2005-503182) and JP-A 2006-068534.

U.S. Pat. Pub. 2005/004474 (corresponding to JP-A 2005-503182) discloses the capsule endoscope including a mirror and other optical elements to photograph a scene of the front or rear or the right or left. JP-A 2006-068534 discloses the capsule endoscope having two image pickup units positioned in the front and rear for alternately picking up and image to prevent missing in imaging recording.

A frame rate, or the number of frames per unit time in the image pickup, is 2 fps (frame per second). Expected total time required for the diagnosis is 8 hours or more. An amount of image data stored in the receiver will be excessively large. If medical staff wishes to read all images after the inspection for diagnosis, there is a problem of requiring considerable time.

The use of the capsule endoscope is characterized in minimized physical stress to the body of the patient in comparison with diagnosis with an endoscope of the widely used steerable type. Enhanced use of the capsule endoscope is expected in the future techniques in the medicine. There is requirement of precision and rapidity in reading images of the target region for observation of lesions recently discovered in the inspection or having had surgical operation.

The use of the multi head type in U.S. Pat. Pub. 2005/004474 (corresponding to JP-A 2005-503182) and JP-A 2006-068534 is effective in preventing missing in the image pickup. Precision in the observation of the target region may be higher than that in the single head type. However, the amount of image data is two times as high as that of the single head type. The reading of the target region cannot be completed in a short time.

SUMMARY OF THE INVENTION

In view of the foregoing problems, an object of the present invention is to provide a capsule endoscope in which plural image pickup units are incorporated, and of which handling of acquired images can be facilitated, and a capsule endoscopic system, and endoscope control method.

In order to achieve the above and other objects and advantages of this invention, a capsule endoscope for endoscopic imaging by passing a gastrointestinal tract in a body includes plural image pickup units for image pickup inside the gastrointestinal tract. A controller determines a number of frames of imaging per unit time for respectively the plural image pickup units according to position relationship information of a position relationship of the image pickup units to a target region in the gastrointestinal tract, to control the plural image pickup units.

The number of the frames is determined according to a frame number ratio of frame numbers and a total frame number of frames optimized previously in consideration of the position relationship information.

Furthermore, a communication interface wirelessly receives a command signal for determining the number of the frames from an external device for data retrieval of image data from the image pickup units. The controller determines the number of the frames according to the command signal.

Furthermore, a data storage stores the number of the frames according to the command signal.

Furthermore, a capsule casing has first and second ends positioned in a longitudinal direction thereof. The image pickup units are first and second image pickup units positioned at respectively the first and second ends. The number of the frames is determined according to which of the first and second image pickup units advances to move in relation to the target region.

Furthermore, a direction detector detects a direction of the image pickup units in the body.

The direction detector includes an acceleration sensor for measuring a capsule acceleration rate in the body. An integrator integrates the capsule acceleration rate.

The number of the frames is set greater for the first image pickup unit than for the second image pickup unit during movement toward the target region by advancing the first image pickup unit, and is set smaller for the first image pickup unit than for the second image pickup unit during movement away from the target region by advancing the first image pickup unit.

The first and second image pickup units create respectively first and second image data. The position relationship data is produced by evaluating the first and second image data and local property data of a radio wave from the communication interface in a time sequential manner.

The controller is operable in one of first and second operation modes related to image pickup of the image pickup units, and when in the first operation mode, operates the image pickup units at the number of the frames based on a condition of the target region, and when in the second operation mode, operates the image pickup units at a time point irrespective of the condition of the target region.

The position relationship data is retrieved according to a present endoscopic output in inspection by referring to diagnostic information stored after extraction from the target region in a past diagnosis.

The diagnostic information includes at least one of image data of the target region, and position information of the target region associated with the image data.

The position information is constituted by at least one of a capsule position, endoscopic operation time, and capsule moving distance upon image pickup of the target region.

The position relationship data is retrieved according to a present endoscopic output in inspection by referring to case information stored after extraction from medically typical cases and related to the target region.

The case information includes image data of at least one of a typical lesion and foreign material.

In one aspect of the invention, a capsule endoscope system includes a capsule endoscope, having plural image pickup units, for endoscopic imaging by passing a gastrointestinal tract in a body, and a receiver for wireless communication with the capsule endoscope, and for receiving and storing image data from the capsule endoscope. In the capsule endoscope system, the receiver includes an information retriever for retrieving position relationship data expressing a position relationship of the image pickup units to a target region in the gastrointestinal tract. A command signal generator produces a command signal according to the position relationship data for determining a number of frames of imaging per unit time for respectively the plural image pickup units. The capsule endoscope includes a controller for controlling operation of the plural image pickup units according to the command signal from the receiver.

The capsule endoscope and the receiver include respectively first and second communication interfaces for wireless communication.

The image pickup units are first and second image pickup units positioned at respectively first and second ends of the capsule endoscope. The capsule endoscope includes a direction detector for detecting a direction of the first and second image pickup units in the body. The command signal generator produces the command signal in response to an output of the direction detector and according to which of the first and second image pickup units advances to move in relation to the target region.

Furthermore, a first data storage stores diagnostic information extracted from the target region in a past diagnosis. The information retriever refers to the diagnostic information to retrieve the position relationship data according to a present endoscopic output obtained by the capsule endoscope in inspection.

Furthermore, there is a managing apparatus including the first data storage, for retrieving and managing the image data from the receiver. The receiver includes a second data storage for storing diagnostic information from the managing apparatus.

Furthermore, a first data storage stores case information extracted from medically typical cases and related to the target region. The information retriever refers to the case information to retrieve the position relationship data according to a present endoscopic output obtained by the capsule endoscope in inspection.

The receiver further includes a property extractor for detecting a radio wave from the first communication interface in a predetermined position on the body, and for extracting local property data of the radio wave. A position detector determines a capsule position of the capsule endoscope according to the local property data. The information retriever produces the position relationship data according to the capsule position.

The first and second image pickup units produce respectively first and second image data. The information retriever evaluates the first and second image data and the capsule position in a time sequential manner to produce the position relationship data.

In another aspect of the invention, an endoscope control method is provided, controlling a capsule endoscope, having plural image pickup units, for endoscopic imaging by passing a gastrointestinal tract in a body. The endoscope control method includes retrieving position relationship data expressing a position relationship of the image pickup units to a target region in the gastrointestinal tract. A number of frames of imaging is determined per unit time for respectively the plural image pickup units according to the position relationship data.

Consequently, handling of acquired images can be facilitated in using the capsule endoscope in which plural image pickup units are incorporated, because the position relationship of the image pickup units to a target region can be monitored suitably.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1:
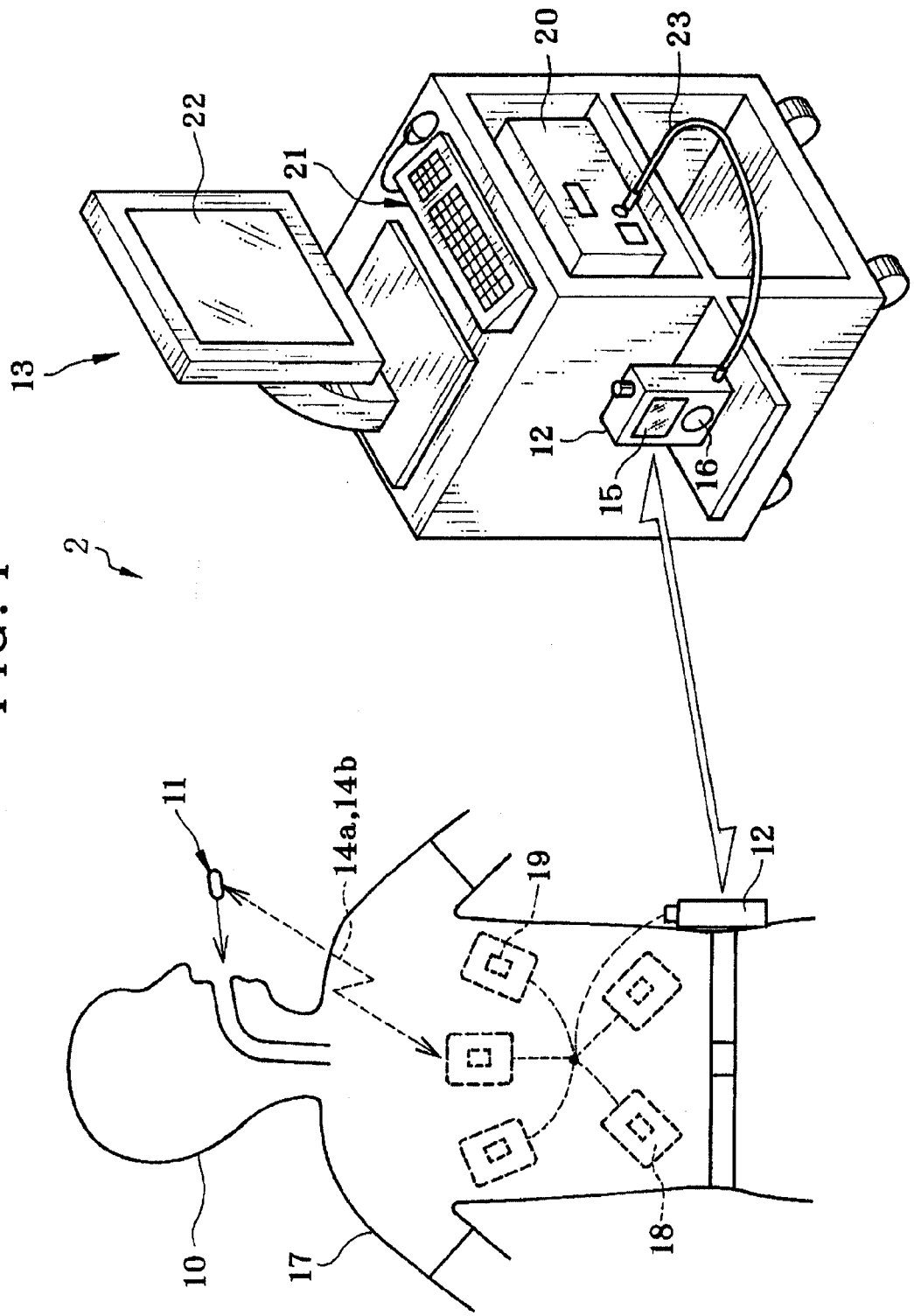
FIG. 1 is an explanatory view illustrating a capsule endoscope.

In FIG. 1, a capsule endoscopic system 2 includes a capsule endoscope 11 or endoscopic imaging capsule, a receiver 12 or communication interface device, and a workstation (WS) 13 or a managing apparatus. The capsule endoscope 11 is orally swallowable in a body 10 of a patient. The receiver 12 is fitted on a belt or the like, and carried by the patient wearing the belt. The workstation 13 processes and records image obtained by the capsule endoscope 11, and is used by medical staff for diagnosis.

The capsule endoscope 11 photographs inner surfaces of a gastrointestinal tract in the body 10. A radio wave 14a is emitted by the capsule endoscope 11 to transmit image data of an image of the gastrointestinal tract wirelessly to the receiver 12. Also, a radio wave 14b for a control command signal is emitted by the receiver 12, and received by the capsule endoscope 11 which operates according to the control command signal.

The receiver 12 includes an LCD display panel 15 and an input panel 16 such as a keyboard and mouse. The LCD display panel 15 displays various menus. The receiver 12 wirelessly receives image data with the radio wave 14a from the capsule endoscope 11, and stores the image data. Also, the receiver 12 produces a control command signal according to diagnostic information of the body 10 of the patient obtained in past diagnosis by use of a capsule endoscope or the like, and wirelessly transmits the control command signal to the capsule endoscope 11 with the radio wave 14b. In short, the capsule endoscope 11 is a slave controlled by the control command signal. The receiver 12 is a master for controlling the capsule endoscope 11 with the control command signal.

For transmission and reception of the radio waves 14a and 14b between the capsule endoscope 11 and the receiver 12, an antenna 42 is disposed in the capsule endoscope 11. See FIGS. 2 and 3. Also, shielding clothes 17 is worn by the body 10 of the patient. Plural antennas 18 are secured to the inside of the shielding clothes 17. Electric field strength detectors 19 or electric field sensors are incorporated in the antennas 18 for measuring the electric field strength of the radio wave 14a from the capsule endoscope 11. A position detector 79 of FIG. 4 is supplied with a result of the detection from the electric field strength detectors 19.

The workstation 13 includes a processor 20, a user interface 21 such as a keyboard and mouse, and a monitor display panel 22. A USB cable 23 as communication line connects the processor 20 with the receiver 12, and transmits data to and from the receiver 12. Note that a system of the communication may be other than USB, and may be an infrared communication, radio communication of a certain type, or the like. During or after the inspection of the capsule endoscope 11, the processor 20 retrieves image data from the receiver 12, for storing and managing the image data for each of patients. Before the inspection, the processor 20 sends diagnostic information to the receiver 12. Also, the processor 20 produces a television image according to the image data, and drives the monitor display panel 22 to display the image.

Figure 2:
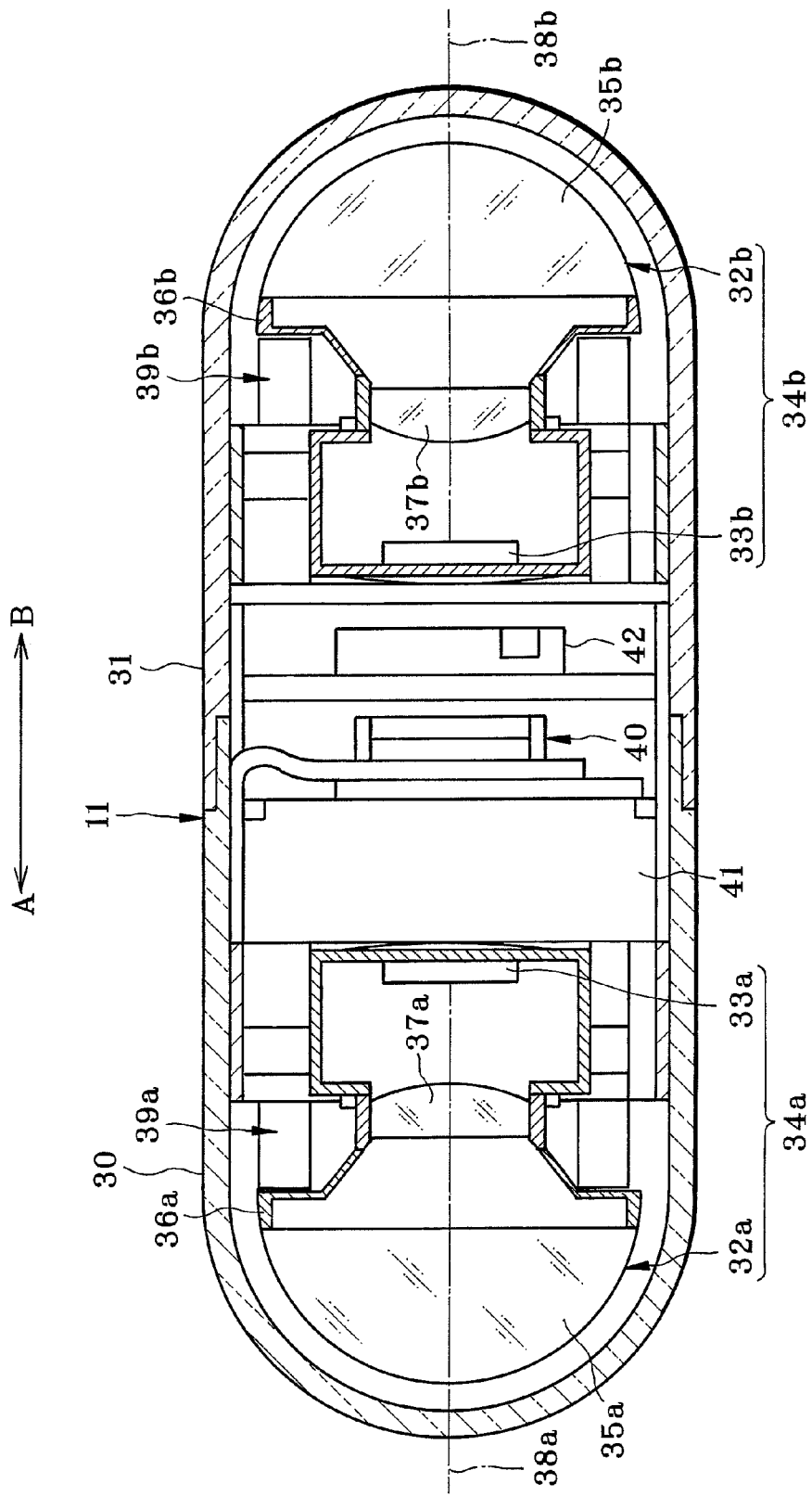
FIG. 2 is a horizontal section illustrating the capsule endoscope.

In FIG. 2, the capsule endoscope 11 of a multi head type includes a transparent front casing 30 and rear casing 31. The rear casing 31 is fitted on the front casing 30 in a watertight manner. A shape of each of the front and rear casings 30 and 31 is a combination of a barrel and a semi spherical portion formed at an end of the barrel.

A camera head or image pickup unit 34a for imaging is contained in the front casing 30, and includes an objective optical system 32a and an image pickup device 33a. The optical system 32a receives object light from a body part as an object. The image pickup device 33a is for example a CCD or CMOS image sensor, and detects the object light to pick up an image of the object. Similarly, a camera head or image pickup unit 34b for imaging is contained in the rear casing 31, and includes an objective optical system 32b and an image pickup device 33b. The image pickup unit 34b is positioned symmetrically with the image pickup unit 34a with reference to the center of the capsule endoscope 11. The image pickup devices 33a and 33b have a sensor surface on which object light from a body part is focused after passage through the optical system 32a or 32b, and output an image signal according to the object light at numerous pixels.

The optical system 32a includes an optical dome 35a or transparent cover, a lens holder 36a and a lens 37a. The optical dome 35a is transparent and convex, and is disposed at the curved end of the front casing 30. The lens holder 36a is fitted on the optical dome 35a and formed with a decreasing width toward the center of the capsule endoscope 11. The lens 37a is supported in the lens holder 36a. In a similar manner, the optical system 32b includes an optical dome 35b or transparent cover, a lens holder 36b and a lens 37b. The optical systems 32a and 32b have a photographable region of 140-180 degrees as angle of view in the forward direction about their optical axes 38a and 38b, and receive object light in any of directions within the photographable region for a target region of a body part. Note that the angle of view is equal between the optical systems 32a and 32b.

Directions A and B are defined herein. The direction A is parallel to the optical axes 38a and 38b and is from the rear casing 31 to the front casing 30. The direction B is reverse to the direction A. If the capsule endoscope 11 travels intraluminally in the direction A, the image pickup device 33a picks up a body part positioned in front. The image pickup device 33b picks up a body part positioned behind. If the capsule endoscope 11 travels intraluminally in the direction B, the image pickup device 33a picks up a body part positioned behind. The image pickup device 33b picks up a body part positioned in front.

Various elements with the image pickup units 34a and 34b are contained in a space inside the front and rear casings 30 and 31, including light sources 39a and 39b, a circuit board 40, a button cell battery 41 and the antenna 42. The light sources 39a and 39b emit light toward a target region of a body part. The circuit board 40 includes mounted circuits such as a communication interface 55 for radio transmission and reception, and a power source circuit 60 of FIG. 3. The antenna 42 transmits and receives the radio waves 14a and 14b.

Figure 3:
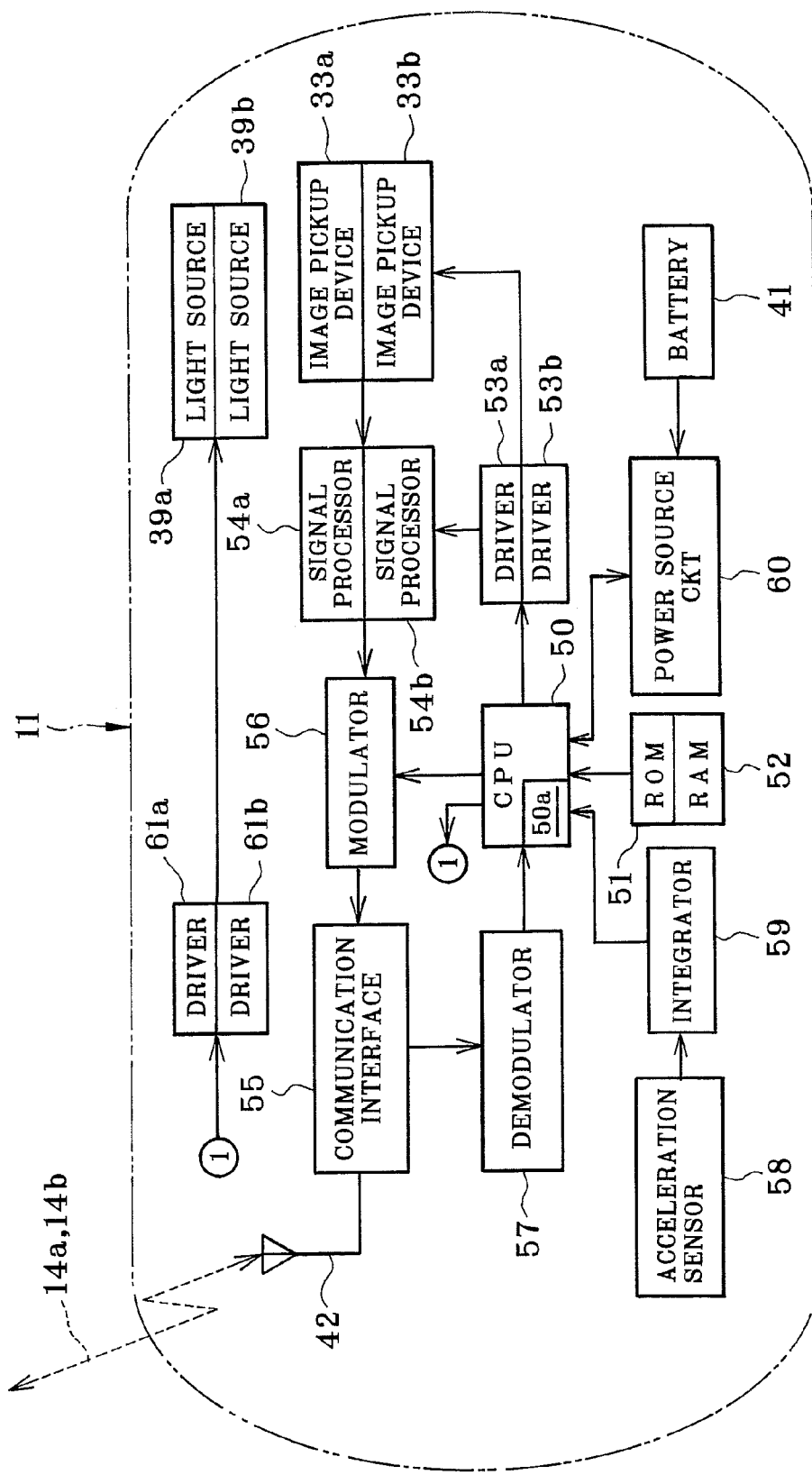
FIG. 3 is a block diagram schematically illustrating circuit elements of the capsule endoscope.
Figure 4:
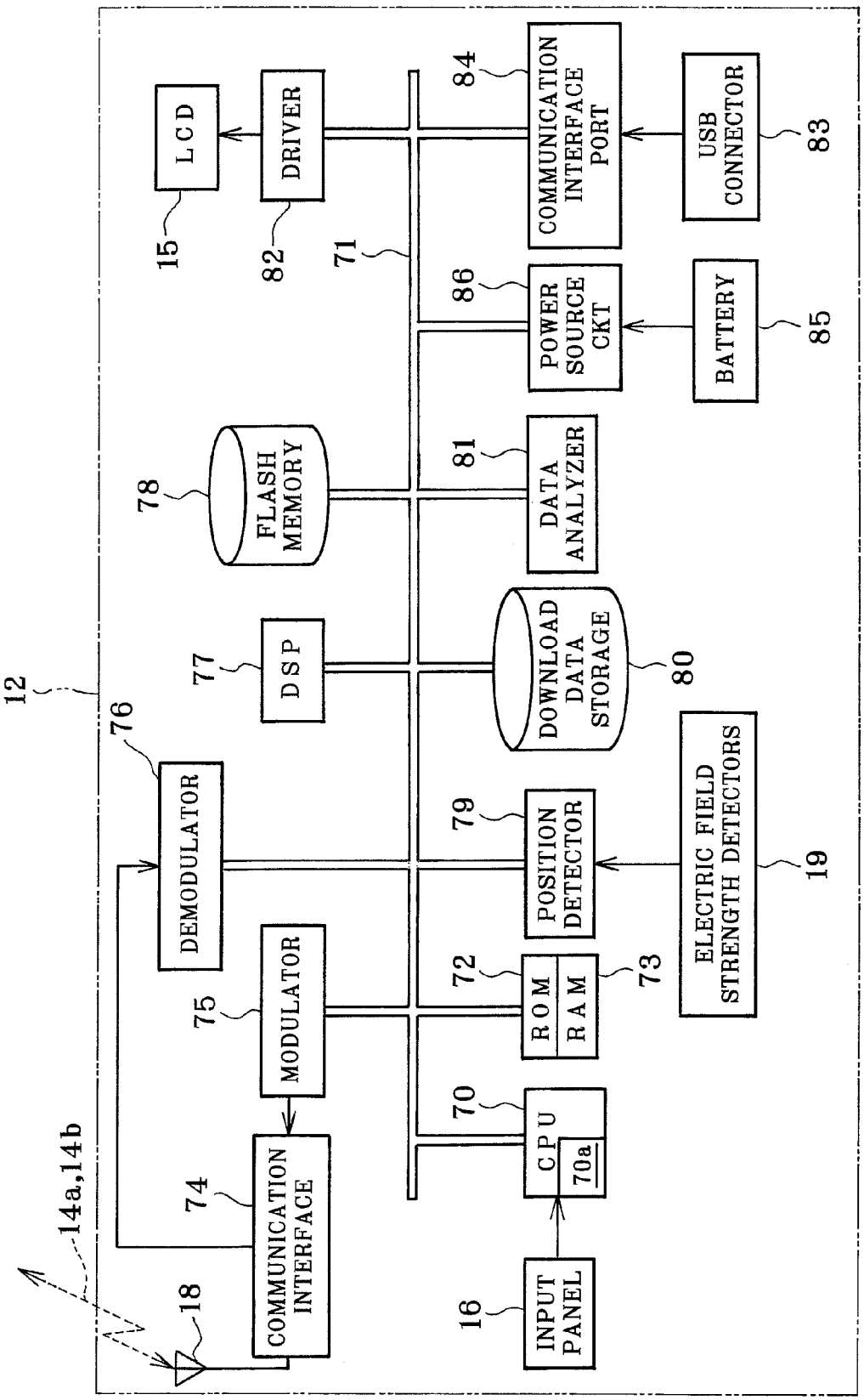
FIG. 4 is a block diagram schematically illustrating a receiver.

In FIG. 3, a CPU 50 controls various elements in the capsule endoscope 11. A ROM 51 and RAM 52 are connected with the CPU 50. The ROM 51 stores programs and data for controlling the capsule endoscope 11. The CPU 50 reads programs and data as required, and executes the programs successively by use of the RAM 52 as working memory in the control. Also, the RAM 52 temporarily stores data of a ratio of the frame number of frames of imaging of the image pickup devices 33a and 33b per unit time, and data of the total frame number of frames of imaging of the image pickup devices 33a and 33b in one second. The ratio is determined according to the control command signal from the receiver 12, and hereinafter referred to as imaging cycle rate (duty factor).

A driver 53a and a signal processor 54a are connected with the image pickup device 33a. A driver 53b and a signal processor 54b are connected with the image pickup device 33b. The drivers 53a and 53b control the image pickup devices 33a and 33b and the signal processors 54a and 54b for imaging at the frame number of imaging according to an imaging cycle rate and the total frame number of imaging. The signal processors 54a and 54b process an image signal from the image pickup devices 33a and 33b in correlated double sampling, amplification and A/D conversion, and convert the image signal into image data of a digital form. The signal processors 54a and 54b process the converted image data by image processing of gamma correction and the like. Note that a second one of the image pickup devices 33a and 33b is inactive while a first one of those operates for imaging. The operation is exclusively selective.

The communication interface 55 is connected with the antenna 42. A modulator 56 and a demodulator 57 are connected with the communication interface 55, and controlled by the CPU 50. Image data of a digital form output by the signal processors 54a and 54b are modulated by the modulator 56 into the radio wave 14a, which is output with the communication interface 55. The demodulator 57 receives the radio wave 14b from the receiver 12, demodulates the radio wave 14b into a control command signal, which is input to the CPU 50. The communication interface 55 amplifies the radio wave 14a from the modulator 56, and filters the radio wave 14a by band-pass filtering. The radio wave 14a is output with the antenna 42. The radio wave 14b, when received by the antenna 42, is amplified by the communication interface 55, is filtered by band-pass filtering, and then is input to the demodulator 57.

An acceleration sensor 58 measures acceleration rate of the capsule endoscope 11 in the directions A and B, and sends a result of the measurement to an integrator 59. The result of the measurement of the acceleration sensor 58 is positive if the capsule endoscope 11 moves in the direction A with an increasing speed, or moves in the direction B with a decreasing speed. The result of the measurement of the acceleration sensor 58 is negative if the capsule endoscope 11 moves in the direction A with a decreasing speed, or moves in the direction B with an increasing speed. If the capsule endoscope 11 moves at a constant speed in the direction A or B, or remains stopped, or moves vertically to the directions A and B, then the acceleration rate detected by the acceleration sensor 58 is zero. The integrator 59 integrates the measured result of the acceleration sensor 58 at one time with a suitable interval of time, to obtain a moving speed of the capsule endoscope 11 in the direction A or B. The integrator 59 inputs data of the moving speed to the CPU 50.

The CPU 50 cumulatively adds up the moving speed successively output by the integrator 59, to obtain a present moving speed of the capsule endoscope 11. When the capsule endoscope 11 travels in the direction A, the moving speed is positive. When the capsule endoscope 11 travels vertically to the direction A or B or stands still, the moving speed is zero. When the capsule endoscope 11 travels in the direction B, the moving speed is negative. Thus, it is possible to detect one of the directions A and B of travel of the capsule endoscope 11 by checking the polarity of the moving speed.

When the polarity of the moving speed changes between the negative and positive signs, the CPU 50 detects a change in the moving direction of the capsule endoscope 11. The CPU 50 supplies the modulator 56 with a signal expressing the change in the moving direction of the capsule endoscope 11. The signal output to the modulator 56 is modulated to obtain the radio wave 14a in a manner similar to the image data. The radio wave 14a is amplified and filtered in the band-pass filtering, and is transmitted by the antenna 42 wirelessly.

The power source circuit 60 supplies various elements in the capsule endoscope 11 with power from the button cell battery 41. Illumination drivers 61a and 61b drive respectively the light sources 39a and 39b in a state controlled by the CPU 50.

In FIG. 4, a CPU 70 controls various elements in the receiver 12. A ROM 72 and a RAM 73 are connected by a data bus 71 with the CPU 70. Programs and data are stored in the ROM 72 for controlling the operation of the receiver 12. The CPU 70 reads the programs and data as required, and executes the programs successively by use of the RAM 73 as working memory in the control. The CPU 70 operates the circuits in the receiver 12 according to instruction signals input with the input panel 16.

A communication interface 74 for radio transmission and reception is connected with the antennas 18. A modulator 75 and a demodulator 76 are connected with the communication interface 74 by the data bus 71. The modulator 75 modulates the control command signal to produce the radio wave 14b, which is input to the communication interface 74. The demodulator 76 demodulates the radio wave 14a from the receiver 12 to produce initial image data and a signal expressing a change of the direction of the capsule endoscope 11. The image data and the signal are output to a DSP (digital signal processor) 77 and the CPU 70. The communication interface 74 amplifies the radio wave 14b from the modulator 75, filters the radio wave 14b in the band-pass filtering, and then outputs the same to the antennas 18. Also, the communication interface 74 amplifies the radio wave 14a received by the antennas 18, filters the radio wave 14a in the band-pass filtering, and inputs the same to the demodulator 76.

The DSP 77 processes the image data demodulated by the demodulator 76. A flash memory 78 is accessed by the DSP 77 to store the processed image data. An example of the flash memory 78 as data storage has a capacity of 1 GB or so. Image data from the DSP 77 are successively written to the flash memory 78.

The position detector 79 responds to the measuring result of the electric field strength of the radio wave 14a as property data according to the electric field strength detectors 19, and detects a present capsule position in the body. The position detector 79 sends a detection result to the flash memory 78 and a data analyzer 81 as position information of the capsule position. The flash memory 78 stores the position information from the position detector 79 in association with image data from the DSP 77. In addition to the position information, the flash memory 78 is accessed in response to a signal input to the CPU 70 for a change in the direction of the capsule endoscope 11, and stores status information in association with the image data, the status information expressing a selected one of the image pickup units 34a and 34b having picked up the image.

As an example of a method of detecting the position of the capsule endoscope 11 in the body of the patient, at first experimental data are prepared for electric field strength distribution of the radio wave 14a with the antennas 18 according to the capsule position. A data table of the experimental data is stored in the ROM 72. The data table is read with an address of the measured result of the electric field strength detectors 19, to retrieve the capsule position.

It is also possible to detect a phase difference of the radio wave 14a as property data, namely a difference value of time of the reach of the radio wave 14a to the antennas 18, in order to detect the position. The phase difference of the radio wave 14a expresses the access data or position relationship or distance between each of the antennas 18 and the capsule endoscope 11. The position detector 79 operates by use of suitable equations, algorithm, data table or the like, and detects the capsule position by converting the phase difference of the radio wave 14a into a distance between each of the antennas 18 and the capsule endoscope 11. It is possible to detect the direction of the reach of the radio wave 14a to at least two of the antennas 18, and to use a method of triangulation with a base line length as a distance between the antennas 18 for the purpose of detecting the capsule position.

A download data storage 80 stores diagnostic information generated by the processor 20. The diagnostic information includes image data and position information, the image data being information of an image of a lesion retrieved in the past inspection of the body 10 of the patient with a capsule endoscope in a periodic inspection as diagnosis in any of definite and probable statuses, the position information being associated with the image data. The diagnosis information may include position information of coordinate data of a body part of the target of surgical operation in the body 10 if the progress after the operation of the body part is observed by use of a capsule endoscope. The position information is input manually with the user interface 21 by medical staff.

The data analyzer 81 as information retriever reads diagnostic information from the download data storage 80. Present position information from the position detector 79 is compared with previous position information which is included in the diagnostic information. Also, the data analyzer 81 compares present image data from the capsule endoscope 11 with previous image data which is included in the diagnostic information. The data analyzer 81 supplies the CPU 70 with signals of results of the comparison of those.

A result of the comparison between the present and previous position information is data expressing access or closeness of the present capsule position to a target body part which has been found a lesion in a diagnosis or operated on surgically. The target body part is referred to herein as target region. The capsule endoscope 11 is the nearer to the target region according to the degree of equality between the present and previous position information. The data analyzer 81 outputs a position evaluation value which is a value of degree of the equality as comparison result between the present and previous position information.

The comparison result between the present image data and the previous image data is data expressing whether a body part imaged presently by the capsule endoscope 11 is near to the target region or not. The capsule endoscope 11 is the nearer to the target region according to the degree of equality between the present and previous image data. The data analyzer 81 outputs an image feature value which is a value of degree of the equality as comparison result between the present and previous image data.

The data analyzer 81 calculates the image feature value by applied use of known techniques of face detection used in the field of digital still camera. Examples of the techniques are suggested in JP-A 2005-284203, U.S. Pat. Pub. 2005/219395 (corresponding to JP-A 2005-286940), and JP-A 2005-156967. Specifically, data of the target region in previous image data is determined as template data. The present image data is checked to detect equality with the template data in the shape, color, form or other characteristics for predetermined search areas of the present image data. The detection is carried out for all the search areas of the present image data by finely changing the size, angle or the like of the search areas. One of the search areas of which the equality is the highest is found the target region, of which an area is determined as an image feature value.

Also, various elements are connected with the data bus 71, including a display driver 82, a communication interface port 84, and a power source circuit 86. The display driver 82 controls the LCD display panel 15. The communication interface port 84 is connected by a USB connector 83 with the processor 20 for transmission and reception of data. The power source circuit 86 supplies circuits in the receiver 12 with power from a battery 85.

Note that the terms of image pickup units F and R are used for image pickup units oriented forward and backwards. Image data F and R are retrieved by respectively the image pickup units F and R. The image feature values F and R are those of respectively the image data F and R.

The CPU 70 as command signal generator produces the control command signal of control according to the position evaluation value and the image feature values F and R. The control command signal is output to the modulator 75. The control command signal is for the purpose of determining the imaging cycle rate of the image pickup units F and R and the total frame number of imaging. For example, the imaging cycle rate is changeable stepwise at three values of 87.5, 50 and 12.5% on the basis of the image pickup unit F. Specifically, 87.5% as imaging cycle rate means that a ratio of the frame number of imaging of one image pickup unit to a total frame number of both image pickup units is 87.5% for the image pickup unit F and 12.5% for the image pickup unit R. Also, the total frame number of imaging is changeable stepwise at 1, 8 and 16 frames. Note that an upper limit of the total frame number of imaging is determined as 16 frames in the embodiment.

Figure 5:
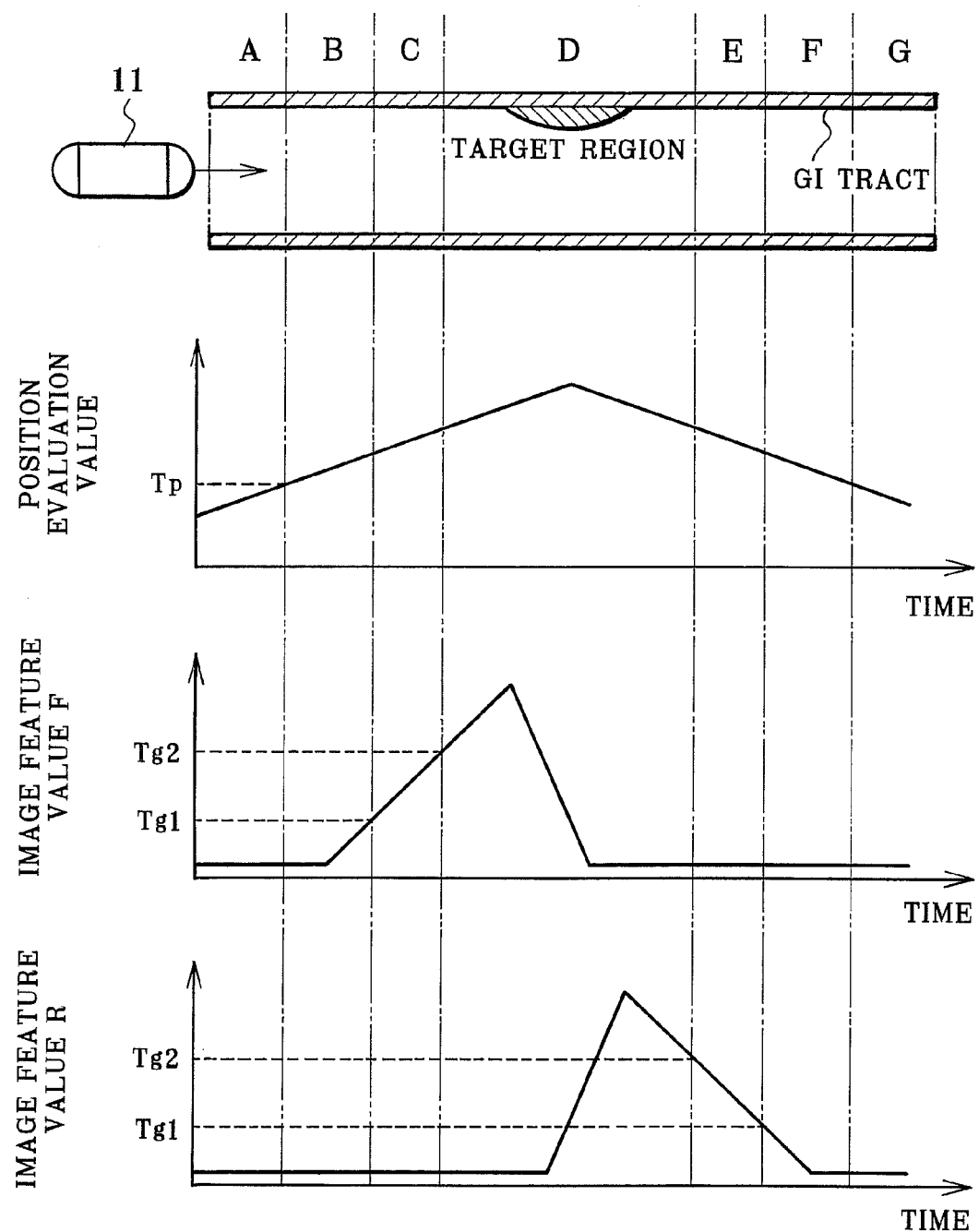
FIG. 5 is a graph illustrating changes of a position evaluation value and an image feature value with time.

In FIG. 5, changes in the position evaluation values and the image feature values F and R are observed. In FIG. 5, the position evaluation value and image feature value change while the capsule endoscope 11 travels through a gastrointestinal tract from a section A to a section G. The section A is short of the target region with a considerable distance. The section B is short of a first half of the target region with a small distance. The section C is before and near to the first half. The section D is position directly at the target region. The section E is after and near to a second half of the target region. The section F is after the second half of the target region with a small distance. The section G is after the target region with a considerable distance.

An example in FIG. 5 is for the purpose of changes of evaluation values with time. It is likely that the evaluation values may change and may be different from the example in FIG. 5 according to the angle of view of the optical systems 32a and 32b, the size of a target region and the like. A quasi target region is herein defined as a region which is between a region distant from the target region and the target region, and which is distant from the target region with at least a predetermined distance. Also, a front side is defined as a downstream side according to the travel of the capsule endoscope 11 from the target region. A rear side is defined as an upstream side according to the travel of the capsule endoscope 11 from the target region.

At first, the position evaluation value is low in the section A, and increases gradually in the sections B and C. In the section D, the present position information is approximately equal to the previous position information. The position evaluation value is the highest. The position evaluation value decreases gradually in the sections E and F, and is low in the section G again in a manner similar to the section A.

The change of the image feature value F is observed now. In the section A, the image feature value is low. In the section B, the image feature value becomes higher when the target region starts being photographed with the image pickup unit F. In a first half of the section D, the image feature value becomes the maximum upon viewing the target region with the entire angle of view of the optical system of the image pickup unit F. Then the image feature value becomes abruptly lower according to the decrease in the area photographable with the image pickup unit F while the target region is becoming offset from the angle of view of the optical system of the image pickup unit F. The image pickup unit F comes not to photograph the target region in a second half of the section D. Then the image feature value becomes low again like the section A.

A curve of the image feature value R is in a form obtained by inversion of the curve of the image feature value F from the right to the left, with respect to the middle point of the section D, namely the position of the target region. In the section A, B and C, the image feature value R is low because no target region is viewed with the image pickup unit R. The target region starts entering the angle of view of the optical system of the image pickup unit R at a point in a first half of the section D. The image feature value R becomes higher abruptly upon the start of photographing the target region. The target region becomes viewed fully in the angle of view of the optical system of the image pickup unit R at a point in a second half of the section D. The image feature value R becomes the highest. Then the image feature value R decreases with a decrease in the area of the target region photographed by the image pickup unit R. In the sections F and G, the image feature value R is low again like that in the sections A-C because no target region is viewed.

In consideration of the above situation, images on or near a target region should be numerous for importance in the diagnosis by minimizing the number of less important images for diagnosis. When the capsule endoscope 11 is located distant from the target region, the total frame number of imaging of the image pickup units is reduced. The frame number of imaging is set equal between the image pickup units. When the capsule endoscope 11 is located exactly on the target region, the total frame number of imaging of the image pickup units is set high. The frame number of imaging is set equal between the image pickup units. When one of the image pickup units F and R of the capsule endoscope 11 starts photographing the target region, the total frame number of imaging of the image pickup units is set high. The frame number of imaging of a first one of the image pickup units is set higher than a second one of those.

Figure 6:
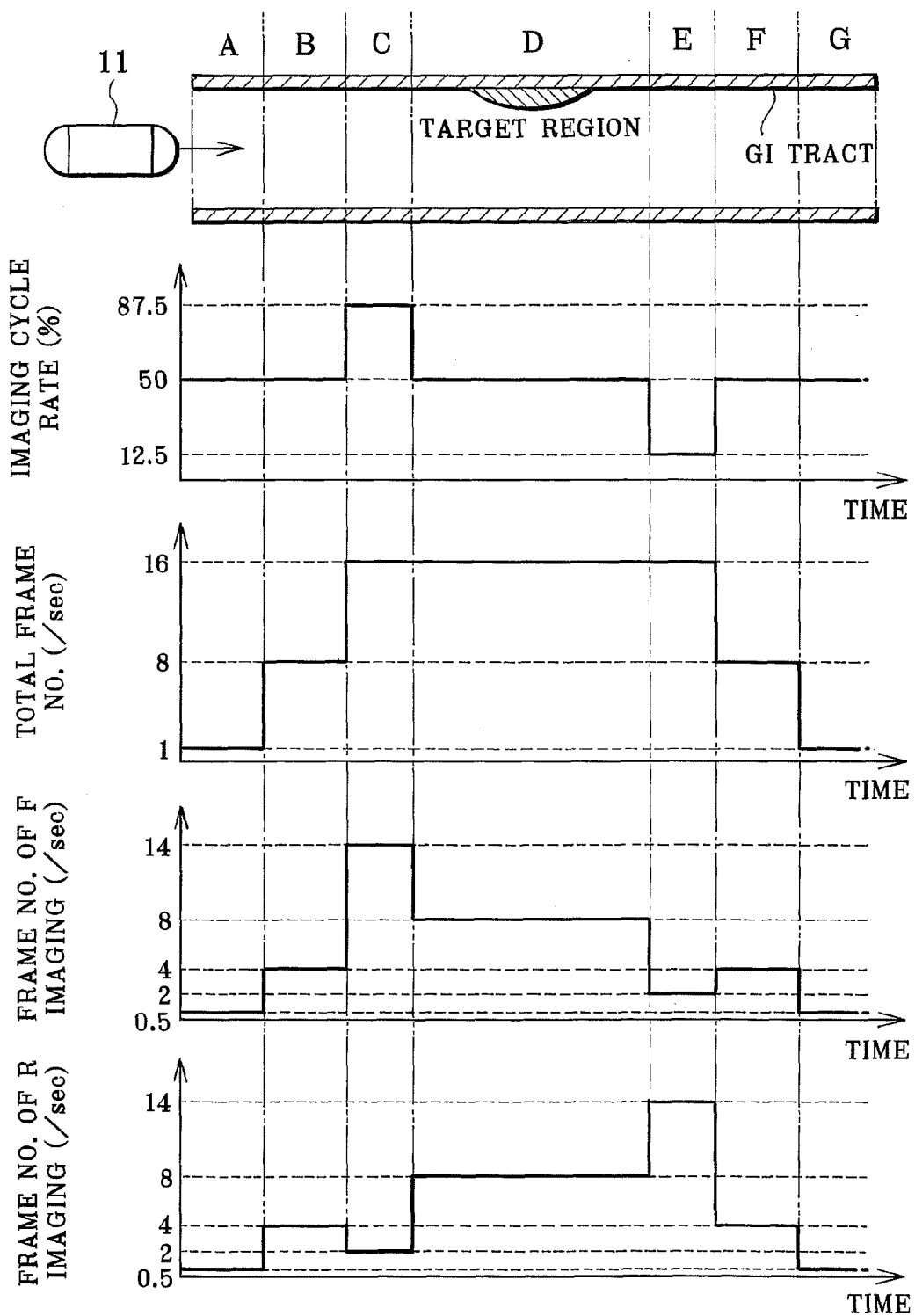
FIG. 6 is a graph illustrating a preferred combination of an imaging cycle rate and a total frame number.

FIG. 6 is referred to now. When the capsule endoscope 11 is positioned short of the section A, both of the position evaluation value and image feature value are low. Then the CPU 70 produces a control command signal to set the imaging cycle rate at 50% and the total frame number of imaging at 1 frame. When the capsule endoscope 11 comes to the section B, the difference obtained by subtracting the threshold Tp (see FIG. 5) from the position evaluation value F becomes positive from the negative value. Then the CPU 70 produces a control command signal to set the imaging cycle rate at 50% and the total frame number of imaging at 8 frames.

When the capsule endoscope 11 comes to the section C, the difference obtained by subtracting the threshold Tg1 from the image feature value F becomes positive from the negative value. Then the CPU 70 produces a control command signal to set the imaging cycle rate at 87.5% and the total frame number of imaging at 16 frames. The threshold value Tp is set at such a level over which a position evaluation value comes when the capsule endoscope 11 is located shorter of the target region than a position (C) where the image feature value comes over the threshold value Tg1.

When the capsule endoscope 11 comes to the section D, the difference obtained by subtracting the threshold Tg2 (>Tg1) from the image feature value F becomes positive from the negative value. Then the CPU 70 produces a control command signal to set the imaging cycle rate at 50% and the total frame number of imaging at 16 frames. When the capsule endoscope 11 comes to the section E, the difference obtained by subtracting the threshold Tg2 from the image feature value R becomes negative from the positive value. Then the CPU 70 produces a control command signal to set the imaging cycle rate at 12.5% and the total frame number of imaging at 16 frames.

When the capsule endoscope 11 comes to the section F, the difference obtained by subtracting the threshold Tg1 from the image feature value R becomes negative from the positive value. Then the CPU 70 produces a control command signal to set the imaging cycle rate at 50% and the total frame number of imaging at 8 frames. Let the capsule endoscope 11 come to the section G. A predetermined length of time has elapsed after setting the imaging cycle rate at 50% and the total frame number of imaging at 8 frames. Then the CPU 70 produces a control command signal to set the imaging cycle rate at 50% and the total frame number of imaging at 1 frame. Note that the imaging cycle rate of the previously determined value, the total frame number of imaging, the elapsed time after determining the setting are stored as data in the RAM 73.

In short, the imaging cycle rate according to the control command signal changes in a sequence of 50, 50, 87.5, 50, 12.5, 50 and 50% in the movement from the section A to the section G. The total frame number of imaging changes in a sequence of 1, 8, 16, 16, 16, 8 and 1 frame. According to the imaging cycle rate and the total frame number, the frame number of imaging of the image pickup unit F changes in a sequence of 0.5, 4, 14, 8, 2, 4 and 0.5 frame. The frame number of imaging of the image pickup unit R changes in a sequence of 0.5, 4, 2, 8, 14, 4 and 0.5 frame.

Figure 7:
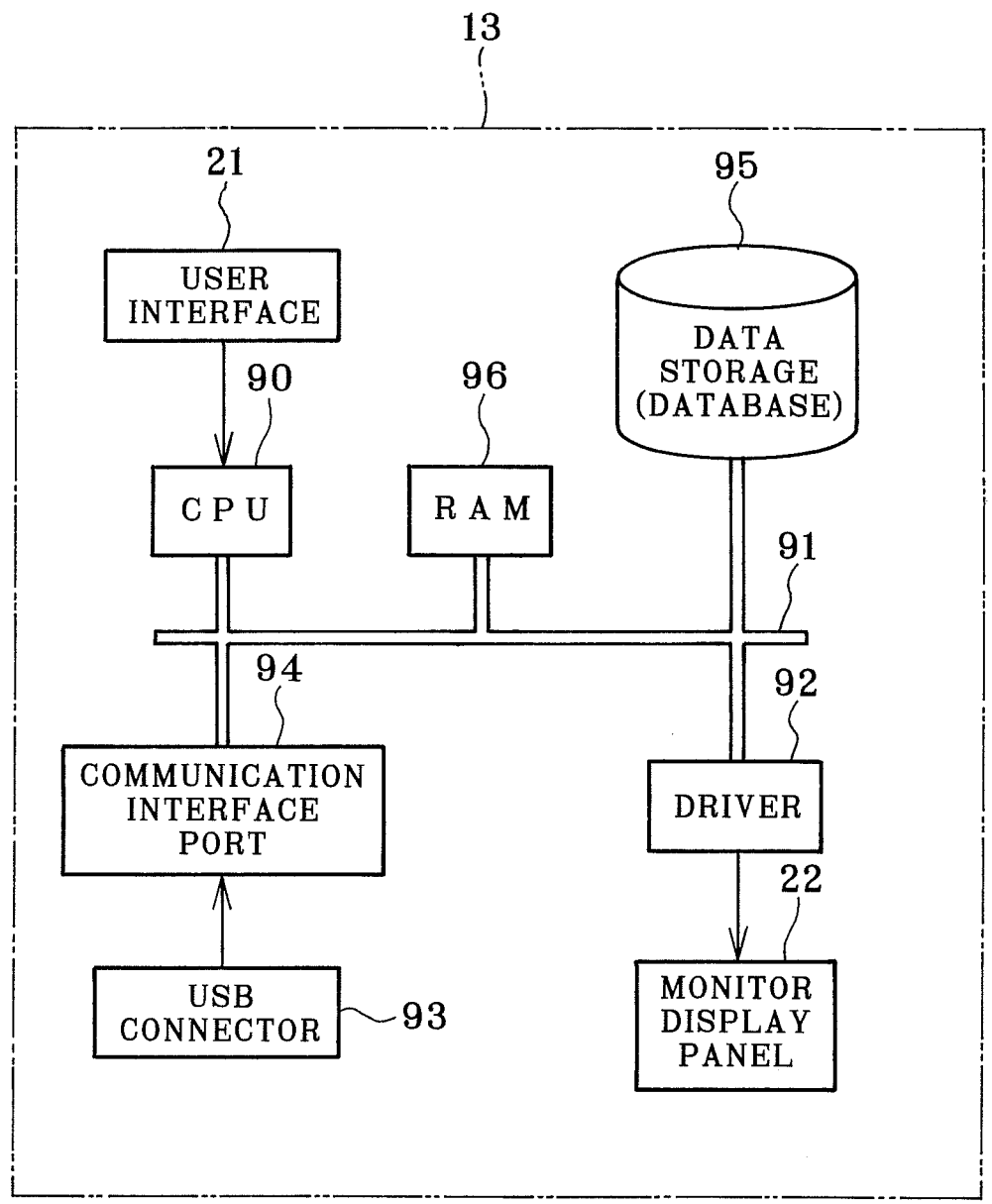
FIG. 7 is a block diagram schematically illustrating circuit elements in a workstation.

In FIG. 7, a CPU 90 controls the entirety of the workstation 13 including various elements. A display driver 92 is connected by a data bus 91 with the CPU 90, and controls the display panel of the monitor display panel 22. A communication interface port 94 is in connection with the receiver 12 by use of a USB connector 93, and operates for receiving image data from the receiver 12 by communication. Also, a data storage 95 or database, and a RAM 96 are connected with the CPU 90.

The data storage 95 is a database storing programs and data for operating the workstation (WS) 13 or managing apparatus, a program of supporting medical diagnosis, and also diagnostic information in a manner sorted discretely for patients. The RAM 96 temporarily stores data read from the data storage 95, intermediate data created in the course of processing, and the like. When the supporting program is started up, a menu pattern for input is displayed on the monitor display panel 22. Medical staff can operate the user interface 21 manually by accessing the menu pattern, to display and edit images, and input diagnostic information and the like.

Figure 8:
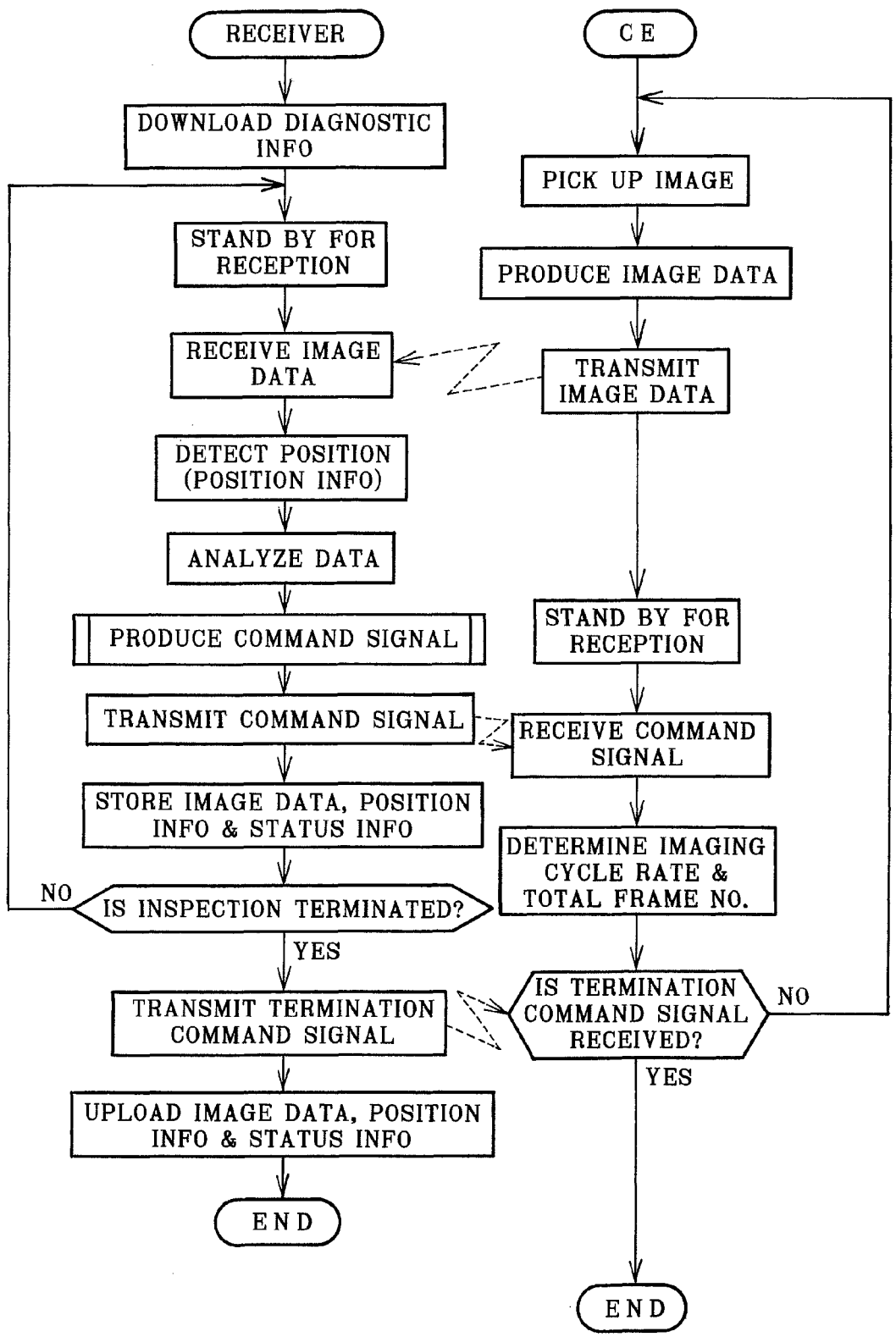
FIG. 8 is a flow chart illustrating a sequence of endoscopic operation.
Figure 9:
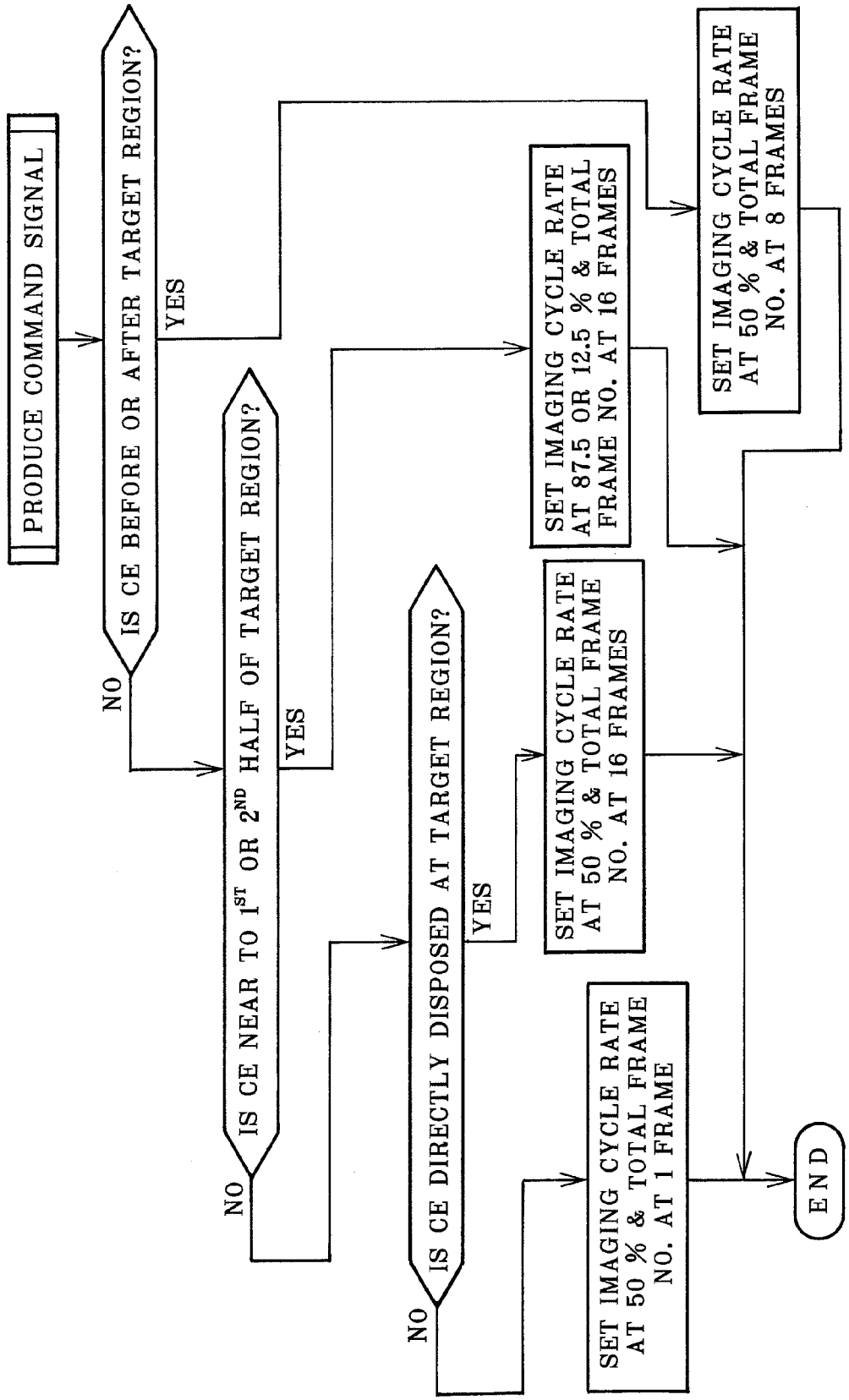
FIG. 9 is a flow chart illustrating a process of producing a control command signal.
Figure 10:
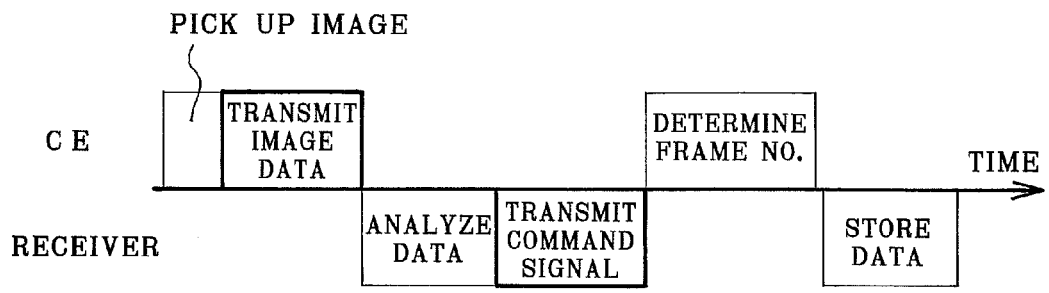
FIG. 10 is a timing chart illustrating the sequence of FIG. 8.

The operation of the inspection with the capsule endoscopic system 2 constructed above is described by referring to FIGS. 8, 9 and 10. At first, the receiver 12 or communication interface device is connected to the processor 20 by the USB cable 23 before the inspection. Diagnosis information of the body 10 of the patient to be inspected is downloaded from the data storage 95 of the workstation 13 to the download data storage 80 of the receiver 12. Then the shielding clothes 17, the receiver 12 and the antennas 18 are set on the body 10. The capsule endoscope 11 is powered, and becomes swallowed by the body 10 in the direction A to his or her gastrointestinal tract.

When the patient orally swallows the capsule endoscope 11, in vivo inspection is ready. The image pickup devices 33a and 33b photograph a gastrointestinal tract in the body 10 with illumination from the light sources 39a and 39b and at 50% for the imaging cycle rate and 1 frame for the total frame number of imaging according to an initial condition. Object light from the target region enters the objective optical systems 32a and 32b, and becomes focused on a detection surface of the image pickup devices 33a and 33b, which output image signals. The image signals output by the image pickup devices 33a and 33b are processed by the signal processors 54a and 54b for the correlated double sampling, amplification and A/D conversion, are converted into image data of a digital form, and are processed in image processing of gamma correction and the like.

Image data of a digital form output by the signal processors 54a and 54b are modulated into the radio wave 14a by the modulator 56. The radio wave 14a is amplified and filtered in the band-pass filtering by the communication interface 55, and is output by the antenna 42 for transmission.

When the antennas 18 receive the radio wave 14a, the communication interface 74 amplifies and filters the radio wave 14a by band-pass filtering. The demodulator 76 demodulates the radio wave 14a to obtain initial image data. The obtained image data is processed by the DSP 77 for signal processing, and is sent to the flash memory 78.

Then the electric field strength detectors 19 measure the electric field strength of the radio wave 14a. According to a result of the measurement of the electric field strength detectors 19, a position of the capsule endoscope 11 in the body is detected by the position detector 79. Position information, namely a detection result of the position detector 79 is output to the flash memory 78 and the data analyzer 81.

Also, an acceleration rate of the capsule endoscope 11 starts being measured by the acceleration sensor 58 soon after swallowing in the body 10 of the patient. Then the direction of the capsule endoscope 11 is detected by the CPU 50 according to the output of the acceleration sensor 58. If the direction of the capsule endoscope 11 changes, a signal expressing the change is transmitted wirelessly by way of the radio wave 14a.

The data analyzer 81 reads diagnostic information from the download data storage 80. The present position information is compared with the previous position information. The present image data is compared with the previous image data. As results of the comparison, the position evaluation value and the image feature values F and R are obtained. Those are input to the CPU 70.

A control command signal is produced by the CPU 70 in the sequence of FIG. 9 according to the position evaluation value and image feature value from the data analyzer 81. When a difference obtained by subtracting a threshold Tp from the position evaluation value becomes positive from the negative value, the CPU 70 produces a control command signal to set the imaging cycle rate at 50% and the total frame number of imaging at 8 frames. Also, when a difference obtained by subtracting a threshold Tg1 from the image feature value R becomes negative from the positive value, the CPU 70 produces the same control command signal. Note that those two situations are in the case of yes for the question step of "IS CE BEFORE OR AFTER TARGET REGION?".

When a difference obtained by subtracting a threshold Tg1 from the image feature value F becomes positive from the negative value, the CPU 70 produces a control command signal to set the imaging cycle rate at 87.5% or 12.5% and the total frame number of imaging at 16 frames. Also, when a difference obtained by subtracting a threshold Tg2 from the image feature value R becomes negative from the positive value, the CPU 70 produces the same control command signal. Note that those two situations are in the case of yes for the question step of "IS CE NEAR TO 1ST OR 2ND HALF OF TARGET REGION?".

When a difference obtained by subtracting a threshold Tg2 from the image feature value F becomes positive from the negative value, the CPU 70 produces a control command signal to set the imaging cycle rate at 50% and the total frame number of imaging at 16 frames. Note that this situation is in the case of yes for the question step of "IS CE DIRECTLY DISPOSED AT TARGET REGION?".

When both of the position evaluation value and image feature value are low, then the CPU 70 produces a control command signal to set the imaging cycle rate at 50% and the total frame number of imaging at one (1) time. Also, when a predetermined time elapses after setting the imaging cycle rate at 50% and the total frame number of imaging at 8 frames, namely in the case of no for the question step of "IS CE DIRECTLY DISPOSED AT TARGET REGION?", then the CPU 70 produces a control command signal to set the imaging cycle rate at 50% and the total frame number of imaging at one (1) time. The determined control command signal is maintained until next occurrence of an event for changing the control command signal, for example when each of the position evaluation value and the image feature values F and R becomes equal to or more than the threshold or becomes equal to or less than the threshold, or when a predetermined time elapses after setting the imaging cycle rate at 50% and the total frame number of imaging at 8 frames.

FIG. 8 is referred to again. The control command signal after setting the imaging cycle rate and the total frame number of imaging by the CPU 70 is modulated into the radio wave 14b by the modulator 75. The radio wave 14b is amplified and filtered in band-pass filtering by the communication interface 74, and is emitted wirelessly by the antennas 18. The receiver 12, upon receiving the control command signal with the radio wave 14b, associates image data from the DSP 77, the position information from the position detector 79 and the status information with one another, and writes those to the flash memory 78.

When the antenna 42 receives the radio wave 14b, the communication interface 55 in the capsule endoscope 11 inputs a signal of the radio wave 14b to the demodulator 57. The radio wave 14b is demodulated by the demodulator 57 into an initial control command signal, which is input to the CPU 50. An imaging cycle rate and total frame number of the image pickup are stored in the RAM 52 in a temporary manner.

The data of the imaging cycle rate and the total frame number of imaging are read from the RAM 52 for the drivers 53a and 53b. The image pickup devices 33a and 33b and the signal processors 54a and 54b are controlled with the drivers 53a and 53b for image pickup at the frame number of imaging depending upon the imaging cycle rate and the total frame number of imaging according to the control command signal. This sequence is continued until transmission of a termination control command signal by the receiver 12 to the capsule endoscope 11 with the radio wave 14b after the inspection.

After the inspection, the processor 20 is connected with the receiver 12 again by the USB cable 23. Image data, associated position information, and status information stored in the flash memory 78 are uploaded in the data storage 95 (database) of the workstation 13. Diagnosis is carried out in the workstation 13 by running a computer program for support.

The sequence at the start of the inspection is illustrated in FIG. 10. At first, an image is picked up in the initial condition of the imaging cycle rate as 50% and the total frame number of imaging as 1 frame. Image data is obtained, and is transmitted to the receiver 12 with the radio wave 14a. The receiver 12 responsive to the radio wave 14a analyzes data and produces a control command signal, which is transmitted to the capsule endoscope 11 in turn with the radio wave 14b.

The capsule endoscope 11 in response to the radio wave 14b stores and determines the imaging cycle rate and the total frame number of imaging according to the control command signal. The imaging cycle rate and the total frame number of imaging are used in the succeeding step of image pickup. Also, the receiver 12 stores image data, position information and status information. In the embodiment, the capsule endoscope 11 photographs a body part in vivo at first. Image data is transmitted by the capsule endoscope 11 toward the receiver 12. After this, a control command signal is produced and transmitted, and imaging cycle rate and the total frame number of imaging are stored and determined. Note that a signal expressing a change of the direction of the capsule endoscope 11 is wirelessly transmitted while no image data is transmitted with the radio wave 14a, and while no control command signal is transmitted with the radio wave 14b.

Figure 11A:
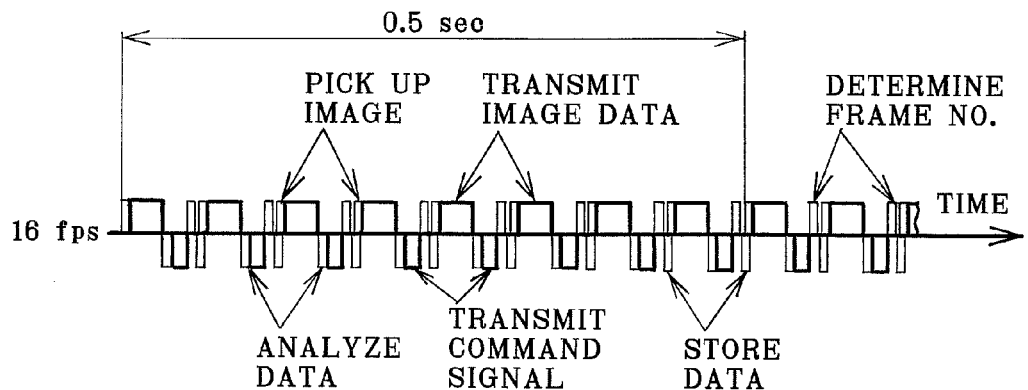
FIG. 11A is a timing chart illustrating an example of the sequence of FIG. 10 in a form viewed more largely.

In FIG. 11A, a sequence of FIG. 10 is repeated for 16 frames regularly in one second, namely for 8 frames in 0.5 second. In the sequence, the capsule endoscope 11 operates for imaging, transmission of image data, and storing of the frame number of imaging. The receiver 12 operates for data analysis, transmission of a control command signal, and storing of data. This is a first operation mode among plural operation modes.

Figure 11B:
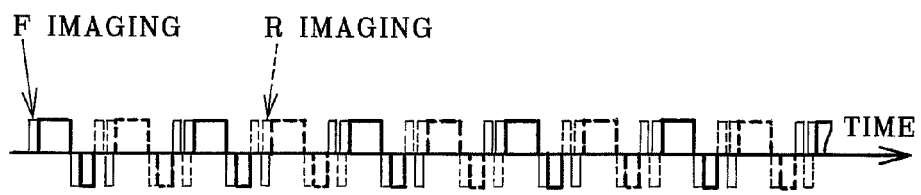
FIG. 11B is a timing chart illustrating the sequence of FIG. 10 in which the imaging cycle rate is 50% and the total frame number is 8 frames.
Figure 11C:
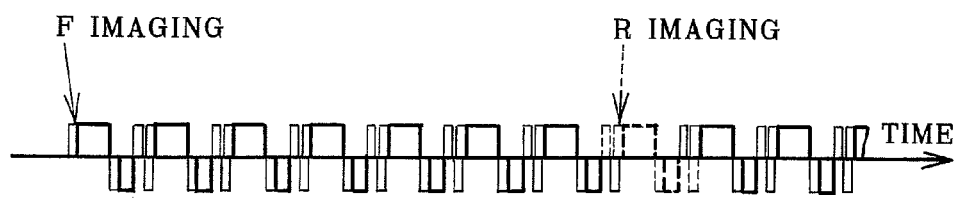
FIG. 11C is a timing chart illustrating the sequence of FIG. 10 in which the imaging cycle rate is 87.5% and the total frame number is 16 frames.

In FIG. 11B, if the imaging cycle rate is set at 50% and the total frame number of imaging is set at 16 frames, then the period of imaging is set alternately at a regular interval for the image pickup unit F (indicated by the solid line) and the image pickup unit R (indicated by the broken line). If the imaging cycle rate is 50% and the total frame number of imaging is one (1) time, then the image pickup units F and R operate for imaging of one frame in two seconds and alternately with one second. In FIG. 11C, if the imaging cycle rate is 87.5% and the total frame number of imaging is 16 frames, then the image pickup unit R operates for imaging of one frame each time when the image pickup unit F operates for imaging of 7 frames.

Consequently, it is possible to reduce the amount of images of body parts not containing a target region to be diagnosed, because the frame number of imaging of the image pickup units F and R is changed according to the access data or position relationship between the capsule endoscope 11 and the target region. An amount of images of the target region to be observed in detail can be greater. Also, an accidental situation of missing images of a target region can be prevented. The feature of the invention is advantageous typically in periodical inspection or post-operation observation of a progress of the target region, because of correct and rapid inspection.

The amount of images of body parts, which are different from the target region and less important in the diagnosis, is reduced. The amount of images handled in the diagnosis is smaller than images obtained when the frame rate is unchanged, so that the load to medical staff can be reduced. Also, the capacity of the flash memory 78 can be smaller in compliance with the smaller amount of images, to reduce the expense for circuit elements in the apparatus. The frame number of imaging can be smaller than when frame rate is unchanged. Thus, power required for image pickup can be kept small, to increase the useful life of the capsule endoscope 11. Note that the amount of images of a target region is greater. However, the target region is only a limited region in a human body. The total amount of images and the frame number of imaging can be effectively set smaller than when the frame rate is unchanged, because the body parts other than the target region are very large.

The capsule endoscope 11 is a slave driven according to the control command signal by the receiver 12 as a master. Thus, the capsule endoscope 11 can have a reduced size without incorporating a specialized circuit like the data analyzer 81 or the like.

In the above embodiment, the imaging cycle rate and the frame number of imaging are determined. However, numbers of frames of imaging for each of the image pickup units F and R can be determined discretely. If the imaging cycle rate and the frame number of imaging are determined with priority, the frame number of imaging for each of the image pickup units F and R is determined uniquely with dependency. However, the discrete determination of the numbers of frames of imaging for each of the image pickup units F and R is effective in having higher degree of freedom in setting the numbers of frames, because there is no dependency on the imaging cycle rate and the frame number of imaging. Note that the frame number of imaging should be set in a range not over the upper limit of the total number of frames, in a manner similar to the above embodiment.

In the above embodiment, the capsule endoscope 11 operates for imaging at the imaging cycle rate and the total frame number of imaging according to the control command signal. In addition to this or in place of this, a control command signal for image pickup may be determined as a release signal for driving one of the image pickup units F and R. When the control command signal is received, a target region can be photographed by the image pickup unit F or R. This is a second operation mode. The processing at the time of the inspection is illustrated in FIGS. 12 and 13, and is different from that of the above embodiment.

Figure 12:
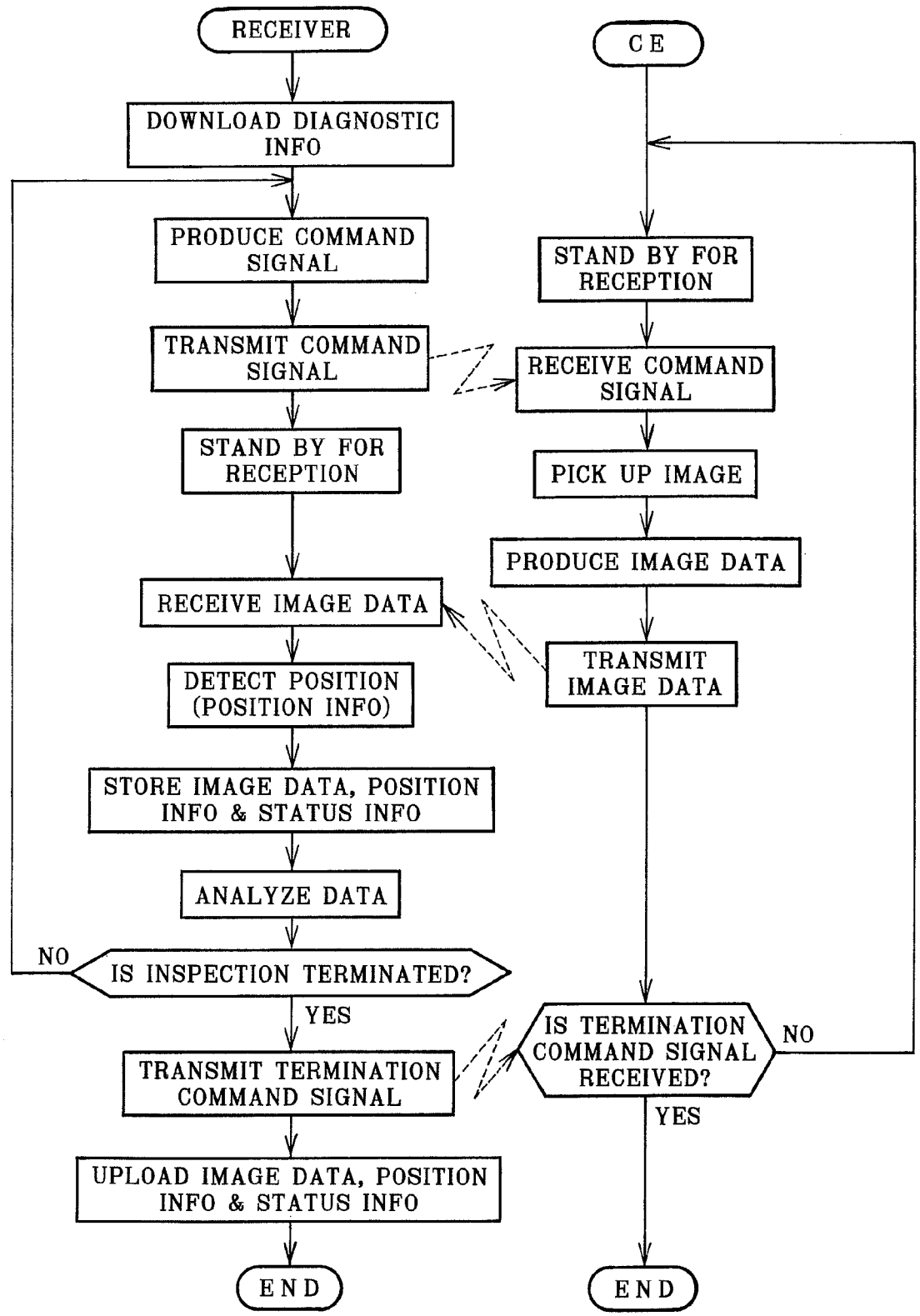
FIG. 12 is a flow chart illustrating a preferred sequence of endoscopic operation in which a control command signal is a release signal.
Figure 13:
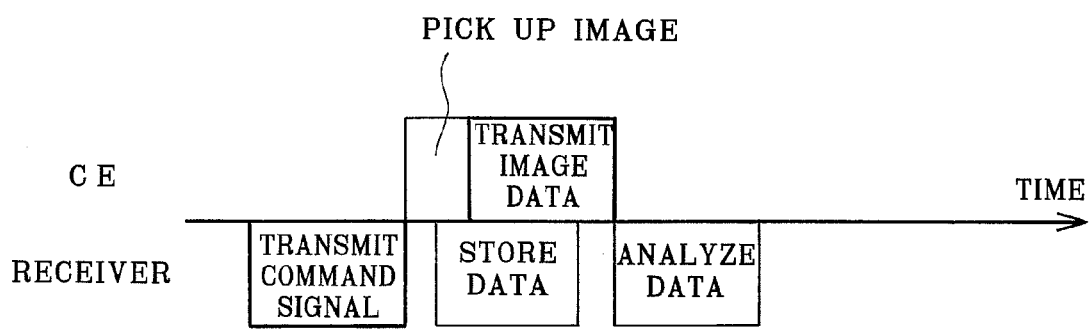
FIG. 13 is a timing chart illustrating the sequence of FIG. 12.

The diagnostic information is downloaded in FIGS. 12 and 13 to stand by for the inspection. Then a control command signal is transmitted with the radio wave 14b by the receiver 12 to the capsule endoscope 11.

When the radio wave 14b is received by the antenna 42, a selected one of the image pickup units F and R immediately operates for imaging of one frame according to designation with the control command signal. Image data is obtained, and transmitted to the receiver 12 with the radio wave 14a. There is no setting of the imaging cycle rate and the total frame number of imaging in the manner of the above embodiment.

The receiver 12 detects the position, stores image data, position information and status information in association, and then carries out the data analysis in the same manner as the above embodiment. A control command signal is produced with data of an interval of time which corresponds to the above-described frame number of imaging determined according to the imaging cycle rate and the total frame number of imaging. The control command signal is transmitted with the radio wave 14b. The capsule endoscope 11 receives the radio wave 14b, and responsively picks up an image for one frame. A sequence of this operation is continued until the transmission of a control command signal of termination, in the same manner as the above embodiment.

Figure 14:
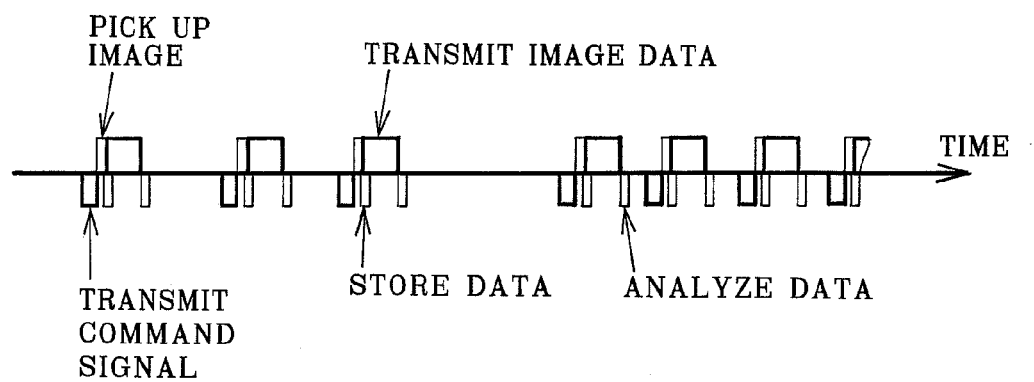
FIG. 14 is a timing chart illustrating the sequence of FIG. 12 in a form viewed more largely.

It is possible as illustrated in FIG. 14 to pick up an image at any suitable interval of time because the control command signal is used as release signal, and is received for triggering the image pickup. This is unlike the above embodiment in which the imaging is carried out at a constant interval of time.

Note that the first and second modes may be used in combination, the first mode being the image pickup at a predetermined interval of time, the second mode being the image pickup at one frame upon receipt of the control command signal. For changeover of the first and second modes, it is possible to use an additional control command signal for switching.

Also, it is possible to disable the image pickup devices 33a and 33b, the drivers 53a and 53b and the signal processors 54a and 54b specifically when imaging is unnecessary, for example if the capsule endoscope 11 is away from a target region for a predetermined time, and if sufficient time is required for the capsule endoscope 11 to reach a succeeding target region. The use of disabling is a third operation mode. To change over the operation to the third operation mode, a control command signal is used. There is no transmission of image data with the radio wave 14a, because of lack of imaging. However, the radio wave 14a is transmitted periodically as beacon signal for detecting the position. Note that the communication interface 55 and the modulator 56 can be disabled, typically if there is no requirement of position detection. A beacon signal may not be transmitted.

In the embodiment, the control command signal is created according to the diagnostic information. This can be used only for patients who were inspected with capsule endoscopes or who had surgical operation before. In addition, it is possible to use case information to produce a control command signal, the case information being obtained from numerous medically typical cases in general. Examples of case information include image data of portions near to lesions of diagnosed patients according to inspection with a capsule endoscope, image data of lesions having feature values of typical shape, color, size and other characteristics, image data of foreign material such as parasitic worms, food particles or the like. In short, case information is characteristic data selected from a great size of data stored after past diagnoses.

The image feature value is determined by comparing the present image data with the image data of the case information in the manner similar to the above embodiment. The CPU 70 produces a control command signal according to the image feature value. There is no determination of a position evaluation value and no production of a control command signal according to a position evaluation value, because no position information is associated with the case information.

Thus, the processing is possible in a manner similar to the production of the control command signal according to the diagnostic information. A new patient without prior inspection can be diagnosed with the capsule endoscope 11. A new lesion without prior discovery can be found, and can be a lesion in a body part other than a target of observation of progress (namely incidental lesion). In the embodiment, the case information is written by the receiver 12 to the download data storage 80, and written by the workstation (WS) 13 or a managing apparatus to the data storage 95 (database). However, additional data storage can be associated with each of the receiver 12 and the workstation 13 for storing case information. For data analysis, the data can be analyzed by the data analyzer 81 in a manner similar to the diagnostic information, or may be an additional analyzer.

A situation is likely to occur that a first one of the image pickup units F and R photographs a target region but a second one of those does not in any time. In relation to the second, a curve of the image feature value is in a form of keeping a low level, which is unlike the curve of FIG. 5, but similar to that in a situation where the capsule endoscope 11 is located away from the target region.

If a difference of subtraction of the threshold value Tg1 from the image feature value F after coming of the image feature value F over the threshold value Tg2 becomes negative, and if the image feature value R is as low as when the capsule endoscope 11 is disposed away from the target region, then it is determined that the image pickup unit F photographs the target region but that the image pickup unit R does not. The imaging cycle rate and the total frame number of imaging are set at 50% and 4 frames for the section F without setting 12.5% and 16 frames for the section E.

If a difference obtained by subtracting the threshold Tg1 from the image feature value R becomes positive, and if the image feature value F remains as low as when the capsule endoscope 11 is away from the target region, then it is found that the image pickup unit R photographs the target region but that the image pickup unit F does not. The imaging cycle rate and the total frame number of imaging are set at 50% and 16 frames in the manner for the section D of the above embodiment.

Also, it is likely that plural target regions exist. Those may be located with a small interval and within one particular section. If the interval is so small that the target regions are photographable at one time with the same angle of view, then the group of the target regions can be regarded as a single target region. Parameters are set for the target region, including the imaging cycle rate, the total frame number of imaging, and the frame numbers of imaging of the image pickup devices F and R. While the capsule endoscope 11 is in the sections C-E, the difference obtained by subtraction of the threshold Tp from the position evaluation value of a succeeding target region may become positive. In case of this, the position evaluation value is ignored. The image pickup of the previous target region is handled with priority.

In the above embodiment, the electric field strength detectors 19 are used for detecting the position information. Instead of this, a magnetic detecting method may be used. A magnet is incorporated in the capsule endoscope 11. Hall elements are associated with the antennas 18, and measure strength of a magnetic field of the magnet, to detect the capsule position within the body by the position detector 79. Furthermore, well-known image recognition can be utilized for position detection without using the electric field strength detectors 19 or magnetic detecting method. An image recognition unit can be incorporated in the receiver 12 for analysis of image data. Image data form the capsule endoscope 11 is analyzed by the image recognition unit to detect a capsule position. For this purpose, template image data is prepared according to images of specific regions of body parts or organs. A capsule position is detected according to degree of equality between the image data from the capsule endoscope 11 and the template image data.

The position of the capsule endoscope 11 may be detected indirectly in place of the direct detection. Time of operation of the capsule endoscope 11 is measured from the start upon swallowing of the capsule endoscope 11, to produce a control command signal according to the measured time instead of or in addition to the directly detected capsule position. To this end, any one of clock circuits 50*a* and 70*a* incorporated in the CPU 50 and 70 is used for the measurement. See FIGS. 3 and 4. It is to be noted that the time can be calculated according to the total frame number of image data if a frame rate is constant in an initial inspection for those image data. The operation time is stored in association with the image data in a manner similar to the above embodiment. At the time of the inspection, a feature value is calculated for expressing degree of coincidence of the presently measured time and the previous operation time being stored. A control command signal is created according to the feature value.

Alternatively, a control command signal can be produced according to a moving distance of the capsule endoscope 11. Upon swallowing the capsule endoscope 11 to start the inspection, measurement of the moving distance is started. The measured moving distance is considered in place of or in addition to the position or operation time, to produce the control command signal. To this end, the acceleration rate measured by the acceleration sensor 58 is integrated by the integrator 59 at two times with a suitable interval. Data of the moving distance of the capsule endoscope 11 is determined, and input to the CPU 50.

The CPU 50 cumulatively adds up the moving distance successively output by the integrator 59, to obtain a total moving distance of the capsule endoscope 11. The moving distance is stored in association with image data in a manner similar to the position and operation time. At the time of the inspection, a control command signal is produced in a manner similar to the position and operation time. It is possible to detect the access data or position relationship between the capsule endoscope 11 and the target region by the combined use of the operation time and moving distance with the capsule position.

Also, it is possible to detect passage of the capsule endoscope 11 through a pylorus of a stomach, namely an exit of the stomach. The time point of the passage at the pylorus may be determined as an origin or zero point for determining the operation time or moving distance instead of the start of the inspection as time point. For this detection, a pH sensor is incorporated in the capsule endoscope 11.

endoscope. Also, passage through the pylorus can be detected by data analysis of image data in the receiver 12 according to image recognition well-known in the art. To this end, precision of the image recognition can be at such a low level as to discern a stomach from other body parts effectively.

The above described methods of detection of the position information are only examples. The invention is not limited to those. Other methods of recognizing the position of the capsule endoscope 11 in a body can be used.

Examples of control command signals are illustrated in Tables 1 and 2.

TABLE 1

| PURPOSE | COMMAND COMPONENT | INDEX NO. | COMPONENT NAME | EXPLANATION |
|---|---|---|---|---|
| POWER SOURCE SYSTEM | 00 | | Reset | RESETTING SYSTEM |
| | 01 | | Wake-up | RETURN FROM Deep Sleep OR Sleep |
| | 02 | | Deep Sleep | WITHOUT BEACON SIGNAL |
| | 03 | | Sleep | WITH BEACON SIGNAL |
| IMAGING SYSTEM | 10 (n) | 1, 2 | Mode | 1: CONSECUTIVE, 2: ONE SHOT |
| | 11 (n) | 1-32 | Total Frame No. | n/2 FRAMES |
| | 12 (n) | 0-8 | Imaging Cycle Rate | n × 12.5% (AS PER F IMAGING) |
| | 13 | | F Release | ONE SHOT OF F IMAGING |
| | 14 | | R Release | ONE SHOT OF R IMAGING |
| | 15 | | F & R Release | ONE SHOT OF F & R IMAGING |
| PRESET | 30 | | Condition 0 | CLOSE-UP, IMAGING CYCLE RATE OF 50% & TOTAL FRAME NO. OF 4 FRAMES |
| | 31 | | Condition 1 | STANDBY, IMAGING CYCLE RATE OF 50% & TOTAL FRAME NO. OF 2 FRAMES |
| | 32 | | Condition 2 | NORMAL, IMAGING CYCLE RATE OF 50% & TOTAL FRAME NO. OF 1 FRAME |
| OTHERS | 40 | | Continuation | NO CHANGE IN CONDITION |
| | 41 (n) | 1-16 | Transmission Power | P = n/16 × Pmax, Pmax AS MAXIMUM NOT OVER STANDARD POWER |

A sensor surface of the pH sensor appears from each of the front and rear casings 30 and 31, and measures a pH value of the gastrointestinal tract in the body 10 to input a result to the CPU 50. When the capsule endoscope 11 passes the pylorus, the output of the pH sensor changes from an acidic condition to a basic condition, because the condition of the stomach is strongly acidic with pH of 1-3 and the condition of the small bowel is basic. The CPU 50 monitors the change in the output of the pH sensor, and outputs a signal with the radio wave 14a for a change from the acid to the base.

When the signal of the change of pH from the acid to the base is received with the radio wave 14a, measurement of the operation time and moving distance is started in the receiver 12 or communication interface device. This is effective in canceling passage time or moving distance inside the stomach, and canceling specificity of patients due to the size of the stomach. Also, the position information specifically in relation to the small bowel and succeeding gastrointestinal organs can be correctly retrieved in the system with the capsule In Table 1, a control command signal includes components for the power source system for power supply to the capsule endoscope 11, components for an imaging system for operation of the image pickup devices 33a and 33b and the signal processors 54a and 54b, preset components for operation conditions, and the like.

Components of the control command signals related to the power source system include:

A component of "Reset". This is command 00, for system resetting of the capsule endoscope 11 upon startup or in case of unexpected failure.

A component of "Deep Sleep". This is command 02, for setting the third operation mode (super low power mode) to suppress transmission of a beacon signal.

A component of "Sleep". This is command 03, for setting the third operation mode (low power mode) with transmission of a beacon signal.

A component of "Wake-up". This is command 01, for setting a normal condition by exiting from the condition of "Deep Sleep" or "Sleep".

The control command signal for the imaging system is constituted by the following components.

A component of "Mode". This is for changeover between a first mode of consecutive imaging at a constant frame rate and a second mode of one shot imaging at one time point, as command 10(n), where n=1 for the first mode and n=2 for the second mode.

A component of "Total frame No.". This is for determining the total frame number of imaging, as command 11(n), where n is 1-32 and the total frame number of imaging is n/2.

A component of "Continuation", command 40 for transmission in case of no change in the operation condition.

A component of "Transmission power", command 41(n) for changing the transmission power of the radio wave 14a, where n is 1-16 and transmission power P=n/16×Pmax, and Pmax is a maximum value of the transmission power not over a standard value of power.

The capsule endoscope 11 detects each one of those components according to the component number of command, and checks the condition according to the index number of the command components.

TABLE 2

| PURPOSE | COMMAND COMPONENT | INDEX NO. | COMPONENT NAME | EXPLANATION |
|---|---|---|---|---|
| POWER SOURCE SYSTEM | 00 | | Reset | RESETTING SYSTEM |
| | 01 | | Wake-up | RETURN FROM Deep Sleep OR Sleep |
| | 02 | | Deep Sleep | WITHOUT BEACON SIGNAL |
| | 03 | | Sleep | WITH BEACON SIGNAL |
| IMAGING SYSTEM | 10 (n) | 1, 2 | Mode | 1: CONSECUTIVE, 2: ONE SHOT |
| | 11 (n) | 1-32 | F Frame No. | n/2 FRAMES |
| | 12 (n) | 1-32 | R Frame No. | n/2 FRAMES |
| | 13 | | F Release | ONE SHOT OF F IMAGING |
| | 14 | | R Release | ONE SHOT OF R IMAGING |
| | 15 | | F & R Release | ONE SHOT OF F & R IMAGING |
| PRESET | 30 | | Condition 0 | CLOSE-UP, 2 FRAMES OF F IMAGING & 2 FRAMES OF R IMAGING |
| | 31 | | Condition 1 | STANDBY, 1 FRAME OF F IMAGING & 1 FRAME OF R IMAGING |
| | 32 | | Condition 2 | NORMAL, 0.5 FRAME OF F IMAGING & 0.5 FRAME OF R IMAGING |
| OTHERS | 40 | | Continuation | NO CHANGE IN CONDITION |
| | 41 (n) | 1-16 | Transmission Power | P = n/16 × Pmax, Pmax AS MAXIMUM NOT OVER STANDARD POWER |

A component of "Imaging cycle rate". This is for determining the imaging cycle rate, as command 12(n), where n is 0-8 and the imaging cycle rate is n×12.5% on the basis of the image pickup unit F.

Components of "F release", "R release" and "F & R release". These are for transmission at one shot imaging as release signals, with "F release" as command 13, for one shot with the image pickup unit F, "R release" as command 14, for one shot with the image pickup unit R, and "F & R release" as command 15, for one shot alternately with the image pickup units F and R.

Preset components of the control command signal include:

A component of "Condition 0". This is command 30, suitable for imaging the target region (50% of the imaging cycle rate, and 4 frames for the total frame number of imaging).

A component of "Condition 1". This is command 31, suitable for imaging a quasi target region (50% of the imaging cycle rate, and 2 frames for the total frame number of imaging).

A component of "Condition 2". This is command 32, suitable for imaging the target region (50% of the imaging cycle rate, and 1 frame for the total frame number of imaging).

Other components of the control command signal include:

An example in Table 2 is a setting of frame number of imaging for the image pickup units F and R without setting the imaging cycle rate and the total frame number of imaging. The command components 11(n) and 12(n) are used for setting the frame number of imaging of the image pickup units F and R. Also, the preset command components of the conditions 0, 1 and 2 are used for setting the frame number of imaging of the image pickup units F and R.

In relation to the command component 12(n) of Table 1, it is possible to set the imaging cycle rate of 0% or 100%. However, no image cycle rate is determined in this command component in a normal situation. The command component is prepared for the image pickup with apparently only one of the units to photograph a target region. The command components 11(n) and 12(n) may be transmitted at each time of image pickup in the manner of the above embodiments, or may be transmitted at a predetermined time interval, for example one second. Also, the command components may be transmitted during a period which extends until the transmission of a succeeding command component. Note that, if the command components 13, 14 and 15 are transmitted, then the image pickup is started immediately. After the image pickup, the capsule endoscope 11 immediately becomes ready for receiving a succeeding command component.

As is well understood from the examples of Tables 1 and 2, the imaging cycle rate, the total frame number of frames of imaging, and the frame number of frames of imaging of the image pickup units F are not limited to the combinations as examples in the above embodiment. For example, if a foreign material is discovered in the data analysis according to case information, the imaging cycle rate may be set at 50% and the total frame number of image may be set at 8 frames at the location of the foreign material. It is further possible to change the values according to specifics of the capsule endoscope 11.

In the embodiment, image data and control command signals are transmitted and received with the antennas, interface circuits and the like in common. However, separate antennas, interface circuits and the like may be used for respectively image data and control command signals.

The methods of data analysis and production of a control command signal, position detection, and direction detection of the capsule endoscope 11 are only examples, and can be modified in the scope of the invention. For example, table data of relationships between an imaging cycle rate, total frame number of imaging, the frame number of imaging of the image pickup units F and R can be prepared experimentally according to a position of a target region in a gastrointestinal tract of a patient and the operation time or moving distance of the capsule endoscope 11. A memory of the capsule endoscope 11 can store the table data, so as to operate the capsule endoscope 11 according to the table data in the inspection.

In the above embodiments, the image pickup units 34a and 34b are positioned at the ends. However, three or more image pickup units may be incorporated. Arrangement of those can be suitably determined, for example, respectively on the lateral sides of the capsule endoscope 11.

The image pickup units 34a and 34b are operated only alternately without simultaneous imaging in the above embodiments, but can be operated for simultaneous imaging. To this end, two sequences of imaging in a consecutive or intermittent manner can be determined for driving the image pickup units 34a and 34b.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A capsule endoscope for endoscopic imaging by passing a gastrointestinal tract in a body, comprising:
    plural image pickup units for image pickup inside said gastrointestinal tract;
    a controller for determining a number of frames of imaging per unit time for respectively said plural image pickup units according to position relationship information of a position relationship of said image pickup units to a target region in said gastrointestinal tract, to control said plural image pickup units,
    wherein said number of said frames is set greater for a first image pickup unit than for a second image pickup unit which is located farther from said target region than said first image pickup unit among said image pickup units when said capsule endoscope approaches said target region, and
    wherein said number of said frames is set greater for said second image pickup unit than for said first image pickup unit when said capsule endoscope leaves said target region,
    wherein said number of said frames is determined according to a frame number ratio of frame numbers and a total frame number of frames optimized previously in consideration of said position relationship information, and
    wherein said frame number ratio of frame numbers optimized previously and said total frame number of frames optimized previously have at least three values respectively.

2. A capsule endoscope as defined in claim 1, further comprising a communication interface for wirelessly receiving a command signal for determining said number of said frames from an external device for data retrieval of image data from said image pickup units;
    wherein said controller determines said number of said frames according to said command signal.

3. A capsule endoscope as defined in claim 2, further comprising a data storage for storing said number of said frames according to said command signal.

4. A capsule endoscope as defined in claim 2, further comprising a direction detector for detecting a direction of a capsule casing in said body.

5. A capsule endoscope as defined in claim 4, wherein said direction detector includes:
    an acceleration sensor for measuring an acceleration rate of a capsule casing in said body; and
    an integrator for integrating said capsule acceleration rate.

6. A capsule endoscope as defined in claim 2, wherein said image pickup units are operable selectively in one of first, second and third operation modes with said controller, and when in said first operation mode, are driven for image pickup at a prescribed time point, and when in said second operation mode, are driven for image pickup at a time point determined arbitrarily, and when in said third operation mode, are stopped from operation of image pickup.

7. A capsule endoscope as defined in claim 2, wherein said position relationship information is retrieved according to a present endoscopic output in inspection by referring to diagnostic information stored after extraction in a past diagnosis.

8. A capsule endoscope as defined in claim 7, wherein said diagnostic information includes at least one of image data of said target region, and position information of said target region associated with said image data.

9. A capsule endoscope as defined in claim 8, wherein said position information is constituted by at least one of a position of a capsule casing, operation time, and moving distance upon image pickup of said target region.

10. A capsule endoscope as defined in claim 2, wherein said position relationship information is retrieved according to a present endoscopic output in inspection by referring to case information stored after extraction from medically typical cases and related to said target region.

11. A capsule endoscope as defined in claim 10, wherein said case information includes image data of at least one of a typical lesion and foreign material.

12. A capsule endoscope as defined in claim 2, further comprising a capsule casing having first and second ends positioned in a longitudinal direction thereof;
    wherein said image pickup units are first and second image pickup units positioned at respectively said first and second ends;
    said number of said frames is determined according to which of said first and second image pickup units advances to move in relation to said target region.

13. A capsule endoscope system, including a capsule endoscope, having plural image pickup units, for endoscopic imaging by passing a gastrointestinal tract in a body, and a receiver for wireless communication with said capsule endoscope, and for receiving and storing image data from said capsule endoscope, said capsule endoscope system comprising:

said receiver including:
an information retriever for retrieving information of a position relationship of said image pickup units to a target region in said gastrointestinal tract;
a command signal generator for producing a command signal according to said position relationship information for determining a number of frames of imaging per unit time for respectively said plural image pickup units;
said capsule endoscope including a controller for controlling operation of said plural image pickup units according to said command signal from said receiver,
wherein said number of said frames is set greater for a first image pickup unit than for a second image pickup unit which is located farther from said target region than said first image pickup unit among said image pickup units when said capsule endoscope approaches said target region, and
wherein said number of said frames is set greater for said second image pickup unit than for said first image pickup unit when said capsule endoscope leaves said target region,
wherein said number of said frames is determined according to a frame number ratio of frame numbers and a total frame number of frames optimized previously in consideration of said position relationship information, and
wherein said frame number ratio of frame numbers optimized previously and said total frame number of frames optimized previously have at least three values respectively.

14. A capsule endoscope system as defined in claim 13, wherein said capsule endoscope and said receiver include respectively first and second communication interfaces for wireless communication.

15. A capsule endoscope system as defined in claim 14, wherein said capsule endoscope includes a direction detector for detecting a direction of a capsule casing in said body;
said information retriever retrieves information as to from which of said image pickup units said image data is obtained in response to an output of said direction detector.

16. A capsule endoscope system as defined in claim 15, further comprising a first data storage for storing diagnostic information extracted in a past diagnosis;
said information retriever refers to said diagnostic information to retrieve said position relationship information according to a present endoscopic output obtained by said capsule endoscope in inspection.

17. A capsule endoscope system as defined in claim 16, further comprising a managing apparatus, including said first data storage, for retrieving and managing said image data from said receiver;
wherein said receiver includes a second data storage for storing diagnostic information from said managing apparatus.

18. A capsule endoscope system as defined in claim 15, further comprising a first data storage for storing case information extracted from medically typical cases and related to said target region;
said information retriever refers to said case information to retrieve said position relationship information according to a present endoscopic output obtained by said capsule endoscope in inspection.

19. A capsule endoscope system as defined in claim 15, wherein said receiver further includes:
a property extractor for detecting a radio wave from said first communication interface in a predetermined position on said body, and for extracting local property data of said radio wave;
a position detector for determining a position of said capsule endoscope in said body according to said local property data;
said information retriever produces said position relationship information according to said capsule position.

20. An endoscope control method of controlling a capsule endoscope, having plural image pickup units, for endoscopic imaging by passing a gastrointestinal tract in a body, said endoscope control method comprising steps of:
retrieving position relationship information of a position relationship of said image pickup units to a target region in said gastrointestinal tract;
determining a number of frames of imaging per unit time for respectively said plural image pickup units according to said position relationship information,
wherein said number of said frames is set greater for a first image pickup unit than for a second image pickup unit which is located farther from said target region than said first image pickup unit among said image pickup units when said capsule endoscope approaches said target region, and
wherein said number of said frames is set greater for said second image pickup unit than for said first image pickup unit when said capsule endoscope leaves said target region,
wherein said number of said frames is determined according to a frame number ratio of frame numbers and a total frame number of frames optimized previously in consideration of said position relationship information, and
wherein said frame number ratio of frame numbers optimized previously and said total frame number of frames optimized previously have at least three values respectively.

* * * * *